US012030920B2

(12) United States Patent
Charlton et al.

(10) Patent No.: US 12,030,920 B2
(45) Date of Patent: *Jul. 9, 2024

(54) RECOMBINANT PROTEINS AND THEIR THERAPEUTIC USES

(71) Applicant: In3Bio Ltd., Hamilton (BM)

(72) Inventors: Keith Alan Charlton, Aberdeen (GB); Erik D'Hondt, Bazel (BE)

(73) Assignee: In3Bio Ltd., Hamilton (BM)

( * ) Notice: Subject to any disclaimer, the term of this patent is extended or adjusted under 35 U.S.C. 154(b) by 120 days.

This patent is subject to a terminal disclaimer.

(21) Appl. No.: 17/521,121

(22) Filed: Nov. 8, 2021

(65) Prior Publication Data

US 2022/0153798 A1   May 19, 2022

Related U.S. Application Data

(63) Continuation of application No. 15/814,723, filed on Nov. 16, 2017, now Pat. No. 11,198,716, which is a continuation of application No. 14/996,553, filed on Jan. 15, 2016, now abandoned, which is a continuation of application No. 13/813,844, filed as application No. PCT/IB2012/002876 on Nov. 21, 2012, now Pat. No. 9,902,760.

(60) Provisional application No. 61/654,401, filed on Jun. 1, 2012, provisional application No. 61/563,128, filed on Nov. 23, 2011.

(51) Int. Cl.

| A61K 39/00 | (2006.01) |
|---|---|
| C07K 14/28 | (2006.01) |
| C07K 14/47 | (2006.01) |
| C07K 14/475 | (2006.01) |
| C07K 14/48 | (2006.01) |
| C07K 14/485 | (2006.01) |
| C07K 14/495 | (2006.01) |
| C07K 14/50 | (2006.01) |
| C07K 14/65 | (2006.01) |
| C07K 14/71 | (2006.01) |
| C12N 9/12 | (2006.01) |
| C12N 9/64 | (2006.01) |

(52) U.S. Cl.
CPC ........ *C07K 14/485* (2013.01); *A61K 39/0005* (2013.01); *A61K 39/0011* (2013.01); *C07K 14/28* (2013.01); *C07K 14/4748* (2013.01); *C07K 14/475* (2013.01); *C07K 14/4753* (2013.01); *C07K 14/48* (2013.01); *C07K 14/495* (2013.01); *C07K 14/50* (2013.01); *C07K 14/65* (2013.01); *C07K 14/71* (2013.01); *C12N 9/12* (2013.01); *C12N 9/6424* (2013.01); *A61K 2039/645* (2013.01); *A61K 2039/70* (2013.01); *C07K 2319/40* (2013.01); *Y02P 20/582* (2015.11)

(58) Field of Classification Search
CPC .................................................. C07K 14/485
See application file for complete search history.

(56) References Cited

U.S. PATENT DOCUMENTS

| 5,894,018 | A | 4/1999 | Davila et al. |
|---|---|---|---|
| 5,984,018 | A | 11/1999 | Yamamoto et al. |
| 7,320,795 | B2 | 1/2008 | Milich et al. |
| 7,763,243 | B2 | 7/2010 | Lum et al. |
| 9,902,760 | B2 | 2/2018 | Charlton et al. |
| 11,198,716 | B2 * | 12/2021 | Charlton ................ C07K 14/48 |
| 2002/0094956 | A1 | 7/2002 | Cosgrove |
| 2003/0176655 | A1 | 9/2003 | Shi et al. |
| 2005/0037967 | A1 | 2/2005 | Rosenblum |
| 2006/0194292 | A1 | 8/2006 | Upton et al. |
| 2006/0246087 | A1 | 11/2006 | Arakawa et al. |
| 2008/0170991 | A1 | 7/2008 | Shi et al. |
| 2008/0176934 | A1 | 7/2008 | Verbeuren et al. |
| 2010/0226923 | A1 | 9/2010 | Rao et al. |
| 2012/0065380 | A1 | 3/2012 | Yoo et al. |

FOREIGN PATENT DOCUMENTS

| CN | 101595219 A | 12/2009 |
|---|---|---|
| EP | 1921149 A1 | 5/2008 |
| EP | 2041177 | 12/2011 |
| JP | H07285883 | 10/1995 |
| JP | 2005052135 A | 3/2005 |
| JP | 2009543071 A | 12/2009 |
| JP | 2010508861 A | 3/2010 |
| JP | 2011187653 A | 9/2011 |
| WO | 2007118660 A2 | 10/2007 |
| WO | 2008005992 A2 | 1/2008 |

(Continued)

OTHER PUBLICATIONS

Kazemi et al (Biotechnology and Environmental Science: Molecular Approaches, pp. 211-218, 1992).
Li. S et al., Pentabody-mediated antigen delivery induces antigen-specific mucosal immune response:, Molecular immunology, Pergamon, GB, vol. 46, No. 8-9, May 1, 2009, pp. 1718-1726.
Jiang Hua et al., "Application of EGFP-EGF fusions to explore mechanism of endocytosis of epidermal growth factor", Acta Pharmacologica Sinica, vol. 28., No. 1, Jan. 2007, pp. 111-117.
Lebens M. et al., a mucosally administered recombinant fusion protein vaccine against schistosomiasis protecting against immunopathology and infection:, Vaccine, Elsevier Ltd., GB, vol. 21., No. 5-6, Jan. 17, 2003.

(Continued)

*Primary Examiner* — Albert M Navarro
(74) *Attorney, Agent, or Firm* — Withers Bergman LLP; John C. Serio

(57) ABSTRACT

A recombinant protein expressing one or more human growth factors, tumor antigens, and/or receptors or epitopes thereof on or within an immunogenic expression creating a recombinant protein in which one or more epitopes are presented on the surface of the sequence in their natural configuration. The growth factor, tumor antigen, and/or receptor, sequence(s) may be expressed within the encoding sequence at appropriate internal positions or at the termini as single expressions or as two or more tandem repeats.

12 Claims, 44 Drawing Sheets

Specification includes a Sequence Listing.

(56) References Cited

FOREIGN PATENT DOCUMENTS

| | | |
|---|---|---|
| WO | 2008058944 A1 | 5/2008 |
| WO | 2012058768 A1 | 5/2012 |

OTHER PUBLICATIONS

Bargou M.D., Ralf C. et al. Sustained Response During Seen after Treatment with Single Agent Blinatumomab MT103/MEDI-538) in the Ongoing Phase I Study MT103-104 in Patients with Relapsed NHL. 50th ASH annual Meeting and Exposition. Dec. 8, 2008. American Society of Hematology. San Francisco, CA.

Dixit, Rakesh, et al. Toxicokinetics and Physiologically Based Toxicokinetics in Toxicology and Risk Assessment. Journal of Toxicology and Environmental Health Part B: Critical Reviews, 6(1): 1-40, 2011.

Lum M.D., Lawrence G. T Cell-Based Immunotherapy for Cancer: A Virtual Reality? CA—A Cancer Journal for Clinicians, 49(2): 74-100, 1999.

Geuijan Cecilia A.W., et al. A Proteomic Approach to Tumour Target Identification Using PH Display, Affinity Purification and Mass Spectrometry. European Journal of Cancer, 41(1): 178-187, 2005.

Dong, Jianying et al. A Stable IgG-like Bispecific Antibody Targeting the Epidermal Growth Factor Receptor and the Type 1 Insulin-like Growth Factor Receptor Demonstrates Superior Anti-Tumor Activity. Landes Bioscience 3(3): 273-288, 2011.

Moore, Paul A. et al. Applicaton of Dual Affinity Retargeting Molecules to Achieve Optimal Redirected Cell Killing of B-cell Lymphoma. Blood Journal. The American Society of Hematology, 117(17): 4542-4551, 2011.

Schoeberl, Birgit. Mathematical Modeling of Signal Transduction Pathways in Mammalian Cells at the Example i the EGF Induced MAP Kinase Cascade and TNF Receptor Crosstalk. Stuttgart, Univ. Diss., 2004.

Mabry, Robert, et al. Engineering of Stable Bispecific Antibodies Targeting IL-17A and IL-23. Protein Engineering, Design & Selection, 23(3): 115-127, 2010.

Strop, Pavel et al. Generating Bispecific Human IgG1 and IgG2 Anitbodies from Any Anitbody Pair. Journal of Molecular Biology, 420(3): 204-219, 2012.

K.N. Srinivasan, P. et al., Scorpion, a Molecular Database of Scorpion Toxins. Toxicon, 40(1 ): 23-31, 2002.

Chu, PhD, Seung Y. et al., Reduction of Total IgE by Targeted Coengagement of IgE B-Cell Receptor and FcyRllb with Fe-Engineered Antibody. Journal of Allergy and Clinical Immunology, 129(4): 1102-1115, 2012.

Zhukovsky E., et al. Recruit-Tandab AFM13—Overcoming Limitations of Monoclonal Antibodies in Hodkin Lymphoma. European Society for Medical Oncology, 23(9): ix350-ix351, 2012.

Wang et al. Cancer Biotherapy & Radiopharmaceuticals vol. 17, No. 6, pp. 665-671, 2002.

Zimmermann et al. Hybridoma vol. 10, No. 1, pp. 65-76, 1991.

Extended European Search Report in corresponding EP application No. 20170470.7 dated Oct. 26, 2020.

Lu, B. et al. Isomers of Epidermal Growth Factor with Ser Cys Mutation at the N-Terminal Sequence: Isomerization, Stability, Unfolding, Refolding, and Structure dated Jul. 18, 2005.

Zhang, Z. et al. Entropic Folding Pathway of Human Epidermal Growth Factor Explored by Disulfide Scrambling and Amplified Collective Motion Simulations dated Jul. 26, 2006.

Stortelers, C. et al. Epidermal Growth Factor Contains Both Positive and Negative Determinants for Interaction with ErbB-2/ErbB-3 Heterodimers dated Nov. 2, 2001.

* cited by examiner

```
NSDSECPLSHDGYCLHDGV CMYIEALDKYA CNCVVGYIGERCQYRDLKWWELR    Human
NSDSECPLSHDGYCLHDGV CMYIEALDKYA CNCVVGYIGERCQYRDLKWWELR    Chimpanzee
NSDSGCPLSHDGYCLHDGV CMYIEALDKYA CNCVVGYIGERCQYRDLKWWELR    Macac
NSNTGCPPSYDGYCLNGGV CMYVESVDRYV CNCVIGYIGERCQHRDLRWWKLR    Brown rat
                    MYVESVDRYV  CNCVIGYIGERCQHRDLRWWNWR    Black rat
NSYPGCPSSYDGYCLNGGV CMHIESLDSYT CNCVIGYSGDRCQTRDLRWWELR    Mouse
NSYSECPPSHDGYCLHGGV CMYIEAVDSYA CNCVFGYVGERCQHRDLKWWELR    Wild boar
NSYQECPPSYDGYCLYNGV CMYIEAVDRYA CNCVFGYVGERCQHRDLK-WELR    Cat
NGYRECPSSYDGYCLYNGV CMYIEAVDRYA CNCVFGYVGERCQHRDLK-WELR    Dog
NSYQECSQSYDGYCLHGGK CVYLVQVDTHA CNCVVGYVGERCQHQDLRWWELR    Horse
       CPPSYESYCLHGGV CNYVSDLQDYA CNCVTGYVGERCQFSDLEWWEQR  Zebra finch
       CPPAYDSYCLHGGV CNYVSDLQDYA CNCVTGYVGERCQFSDLEWWE    Chicken
     ECPLAYDGYCLNGGV CIHFPELKDYG CRCVAGYVGERCQFDDLKSWE     Frog
NGVQSCPSTHDSYCLYDGV CFYFPEMESYA CNCVLGYMGERCQFSDLEWWELQ   Zebra fish
     CPPRYEGFCLHGGI CFYVDRLG-VGCSCPVMYEGERCQY              Lancelet
```

(box labeled 100 surrounding middle column)

FIG. 1

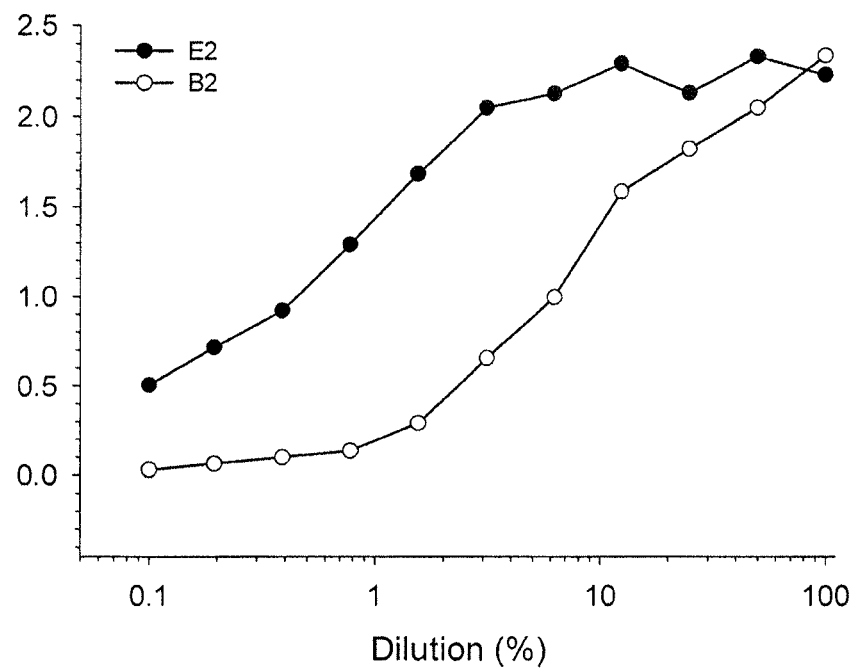
FIG. 11
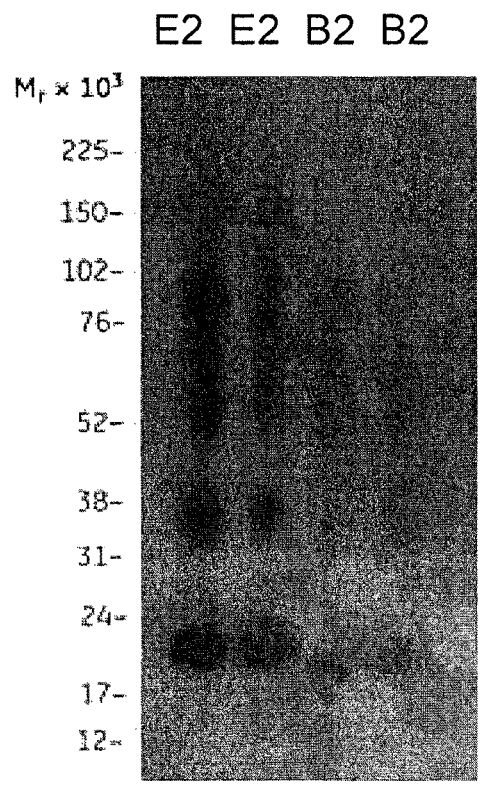

HHHHHHIEGR<u>NSDSECPLSHDGYCLHDGVCMYIE</u>
<u>ALDKYACNCVVGYIGERCQYRDLKWWELR</u>SGG*TPQN*
*ITDLCAEYHNTQIHTLNDKIFSYTESLAGKREMAIITFKN*
*GATFQVEVPGSQHIDSQKKAIERMKDTLRIAYLTEAKVE*
*KLCVWNNKTPHAIAAISMANS*SG<u>NSDSECPLSHDGYCL</u>
<u>HDGVCMYIEALDKYACNCVVGYIGERCQYRDLKWW</u>
<u>ELR</u>

FIG. 13

HHHHHHIEGR<u>CMYIEALDKY</u>SGG*TPQNITDLCAE*
*YHNTQIHTLNDKIFSYTESLAGKREMAIITFKNGATFQV*
*EVPGSQHIDSQKKAIERMKDTLRIAYLTEAKVEKLCVW*
*NNKTPHAIAAISMANSSG*<u>CMYIEALDKY</u>

FIG. 14

HHHHHHIEGR<u>CPLSHDGYCLHDGVCMYIEALDK
YAC</u>SGG*TPQNITDLCAEYHNTQIHTLNDKIFSYTESLAG
KREMAIITFKNGATFQVEVPGSQHIDSQKKAIERMKDT
LRIAYLTEAKVEKLCVWNNKTPHAIAAISMANSSG*<u>CPLS
HDGYCLHDGVCMYIEALDKYAC</u>

| Construct | Sequence |
|---|---|
| T1 | EGF fused directly to the N-terminus of CT-B. |
| T2 | EGF fused to the N-terminus of CT-B and separated from the CT-B by 3 amino acid linkers. |
| T3 | EGF fused to the N-terminus of CT-B and separated from the CT-B by 5 amino acid linkers. |
| T4 | EGF fused directly to the C-terminus of CT-B. |
| T5 | EGF fused to the C-terminus of CT-B and separated from the CT-B by 3 amino acid linkers. |
| T6 | EGF fused to the C-terminus of CT-B and separated from the CT-B by 5 amino acid linkers. |
| E2 | Full length EGF at both termini of CT-B each separated from the CT-B by 3 amino acid linkers. |
| B2 | Truncated EGF (for example, the EGF sequence from Cys6 to Cys31) at both termini of CT-B each separated from the CT-B by 3 amino acid linkers. |

FIG. 17

HHHHHHIEGR<u>GPETLCGAELVDALQFVCGDRGF
YFNKPTGYGSSSRRAPQTGIVDECCFRSCDLRRLEMY
CAPLKPAKSAGSSG</u>*NSDSECPLSHDGYCLHDGVCMYIE
ALDKYACNCVVGYIGERCQYRDLKWWELR*GGSGGTSG
GGGGSG*TPQNITDLCAEYHNTQIHTLNDKIFSYTESLAG
KREMAIITFKNGATFQVEVPSQHIDSQKKAIERMKDTLR
IAYLTEAKVEKLCVWNNKTPHAIAAISMAN*

FIG. 24

HHHHHHIEGR*TPQNITDLCAEYHNTQIHTLNDKIFSYTE*
*SLAGKREMAIITFKNGATFQVEVPSQHIDSQKKAIERMK*
*DTLRIAYLTEAKVEKLCVWNNKTPHAIAAISMANS*SG <u>GP</u>
<u>ETLCGAELVDALQFVCGDRGFYFNKPTGYGSSSRRAP</u>
<u>QTGIVDECCFRSCDLRRLEMYCAPLKPAKSA</u>

FIG. 26 a) mTGF-Beta1

HHHHHHIEGR*TPQNITDLCAEYHNTQIHTLNDKII*
*SYTESLAGKREMAIITFKNGATFQVEVPGSQHIDSQKK*
*IERMKDTLRIAYLTEAKVEKLCVWNNKTPHAIAAISMAN*
SSG<u>ALDTNYCFSSTEKNCCVRQLYIDFRKDLGWKW</u>
<u>HEPKGYHANFCLGPCPYIWSLDTQYSKVLALYNQH</u>
<u>PGASASPCCVPQALEPLPIVYYVGRKPKVEQLSNMI</u>
<u>RSCKCS</u> b) mFGF2

HHHHHHIEGR*TPQNITDLCAEYHNTQIHTLNDKIFSYTI*
*SLAGKREMAIITFKNGATFQVEVPGSQHIDSQKKAIERN*
*KDTLRIAYLTEAKVEKLCVWNNKTPHAIAAISMAN*SSG
<u>ALPEDGGAAFPPGHFKDPKRLYCKNGGFFLRIHPDGI</u>
<u>VDGVREKSDPHVKLQLQAEERGVVSIKGVCANRYL</u>
<u>MKEDGRLLASKCVTEECFFFERLESNNYNTYRSRKY</u>
<u>SWYVALKRTGQYKLGSKTGPGQKAILFLPMSAKS</u> c) mHGF

HHHHHH<u>QKKRRNTLHEFKKSAKTTLTKEDPLLKIK</u>
<u>KKVNSADECANRCIRNRGFTFTCKAFVFDKSRKRC</u>
<u>WYPFNSMSSGVKKGFGHEFDLYENKDYIRNCIIGKG</u>
<u>SYKGTVSITKSGIKCQPWNSMIPHEHSFLPSSYRGKD</u>
<u>QENYCRNPRGEEGGPWCFTSNPEVRYEVCDIPQCSG</u>
SGGTSGGGGSGG*TPQNITDLCAEYHNTQIHTLNDKIF*
*YTESLAGKREMAIITFKNGATFQVEVPGSQHIDSQKKA*
*ERMKDTLRIAYLTEAKVEKLCVWNNKTPHAIAAISMAN* d) mIGF-1/2

FIG. 28

HHHHHHIEGR*TPQNITDLCAEYHNTQIHTLNDKIF*
*SYTESLAGKREMAIITFKNGATFQVEVPGSQHIDSQKKA*
*IERMKDTLRIAYLTEAKVEKLCVWNNKTPHAIAAISMAN*
SSG<u>GPETLCGAELVDALQFVCGPRGFYFNKPTGYGSS</u>
<u>IRRAPQTGIVDECCFRSCDLRRLEMYCAPLKPTKAA</u>
GGS<u>AYGPGETLCGGELVDTLQFVCSDRGFYFSRPSSR</u>
<u>ANRRSRGIVEECCFRSCDLALLETYCATPAKSE</u> e) mVEGF-A/C

HHHHHHIEGR*TPQNITDLCAEYHNTQIHTLNDKIF*
*SYTESLAGKREMAIITFKNGATFQVEVPGSQHIDSQKKA*
*IERMKDTLRIAYLTEAKVEKLCVWNNKTPHAIAAISMA*
*N*<u>SSGVIKFMDVYQRSYCRPIETLVDIFQEYPDEIEYIFK</u>
<u>PSCVPLMRCAGCCNDEALECVPTSESNITMQIMRIKP</u>
<u>HQSQHIGEMSFLQHSRCECRPKK</u>*TEILKSIDNEWRKTQ*
*CMPREVCIDVGKEFGAATNTFFKPPCVSVYRCGGCNS*
*EGLQCMNTSTGYLSKTLFEITVPLSQGPKPVTISFANHT*
*SCRCMS*

FIG. 28 (contd.)

a) HuTGF-Beta1
HHHHHH<u>ALDTNYCFSSTEKNCCVRQ LYIDFRKD
LGWKWIHEPKGYHANFCLGPCPYIWSLDTQYSKVLA
LYNQHNPGASAAPCCVPQALEPLPIVYYVGRKPKVE
QLSNMIVRSCKCS</u>GGSGGTSGGGGGSG*TPQNITDLCA
EYHNTQIHTLNDKIFSYTESLAGKREMAIITFKNGATFQ
VEVPSQHIDSQKKAIERMKDTLRIAYLTEAKVEKLCVWN
NKTPHAIAAISMAN* b) Hu-TGF-Beta-R2
HHHHHHIEGR<u>AVKFPQLCKFCDVRFSTCDNQKSC
MSNCSITSICEKPQEVCVAVWRKNDENITLETVCHDP
KLPYHDFILEDAASPKCIMKEKKKPGETFFMCSCSSD
ECNDNIIFSE</u>GGSGGTSGGGGGSG*TPQNITDLCAEYHN
TQIHTLNDKIFSYTESLAGKREMAIITFKNGATFQVEVP
SQHIDSQKKAIERMKDTLRIAYLTEAKVEKLCVWNNKTP
HAIAAISMAN*

FIG 31 a)
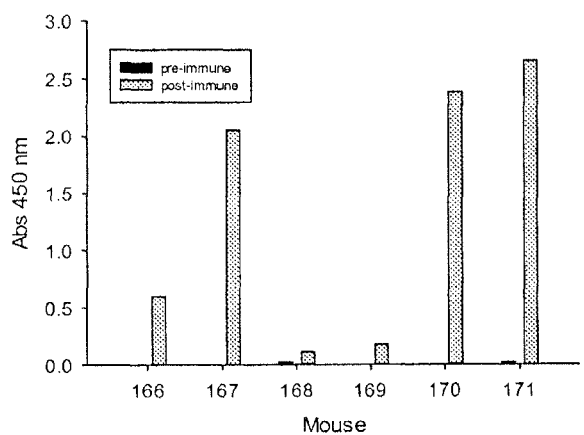
b)
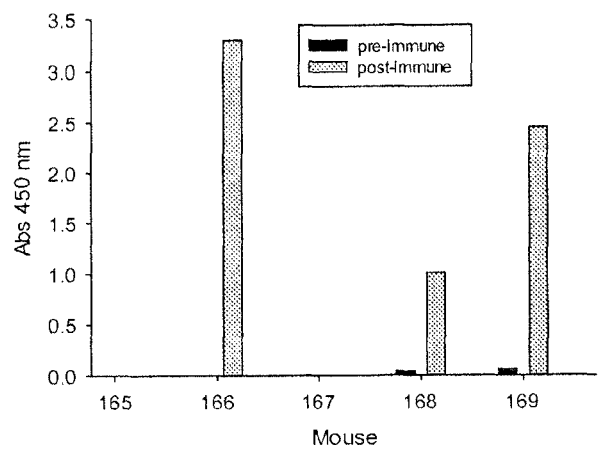
FIG. 36 a) Binding of Group 3 Sera at 1/100 dilution to rHu-IGF
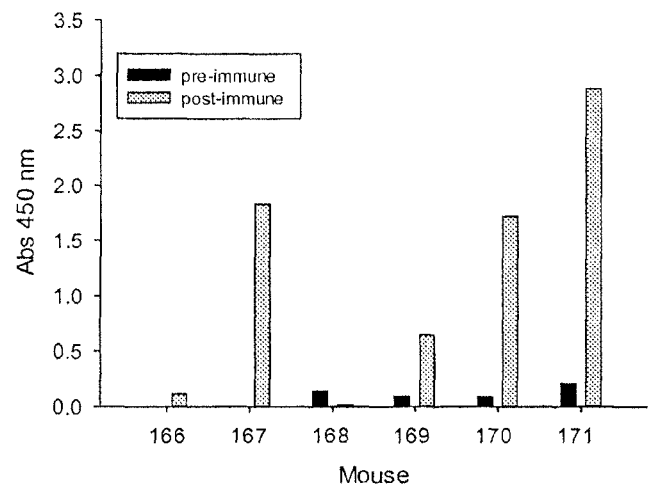
b)
Binding of group 3 Sera at 1/8 dilution to rHu-IGF
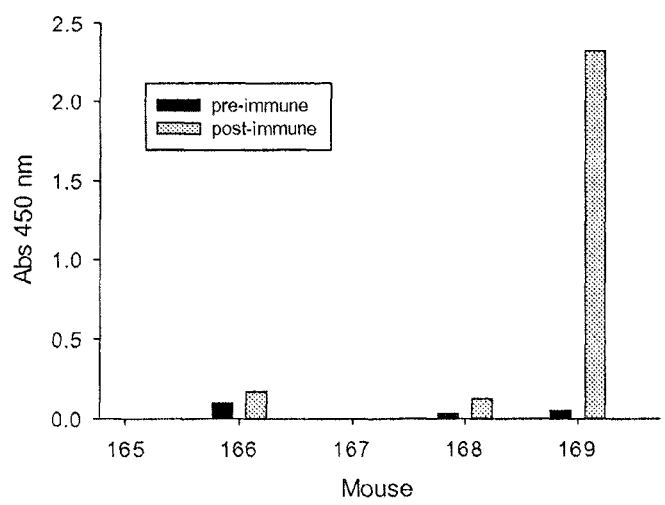
FIG. 37

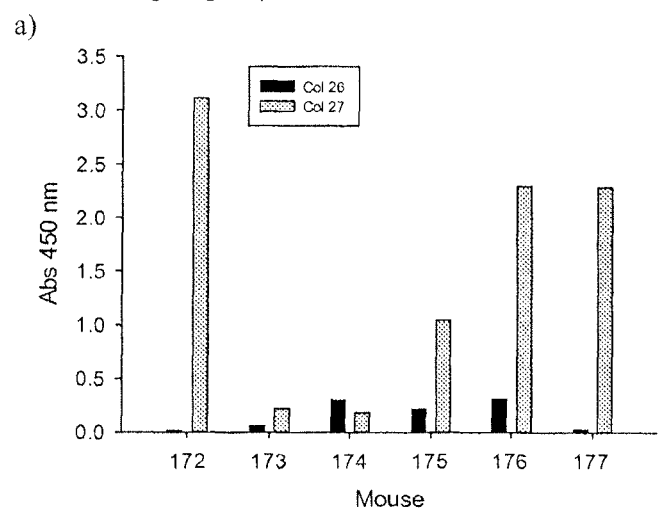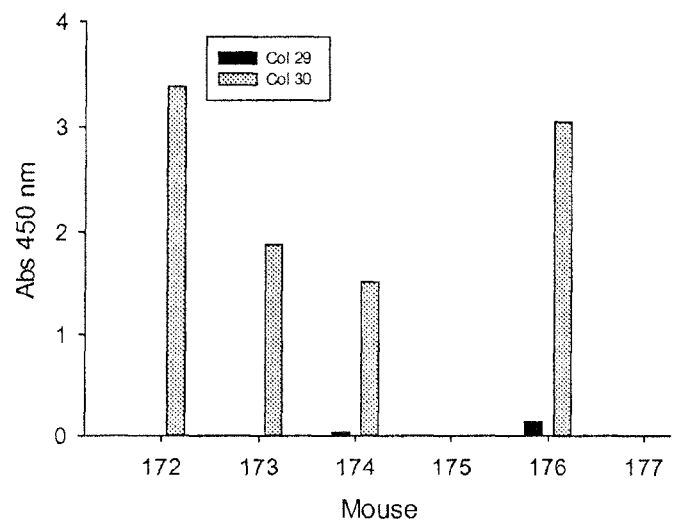
FIG. 38 a) Binding of Group 4 Sera at 1/100 dilution to rHu-IGF
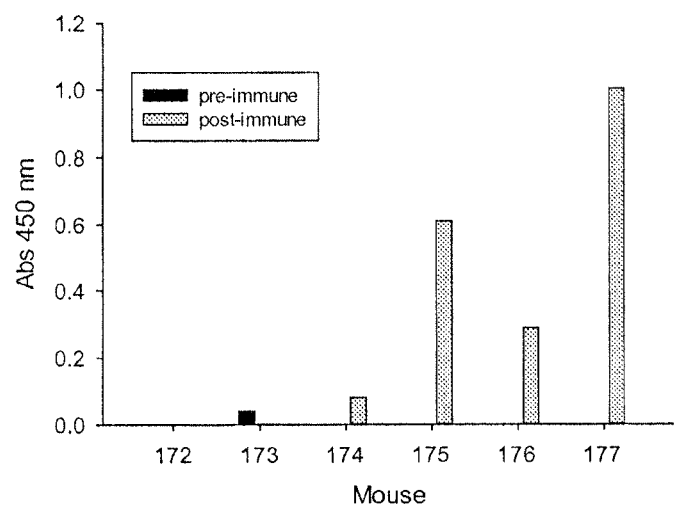
b)
Binding of Group4 Sera at 1/8 dilution to rHu-IGF
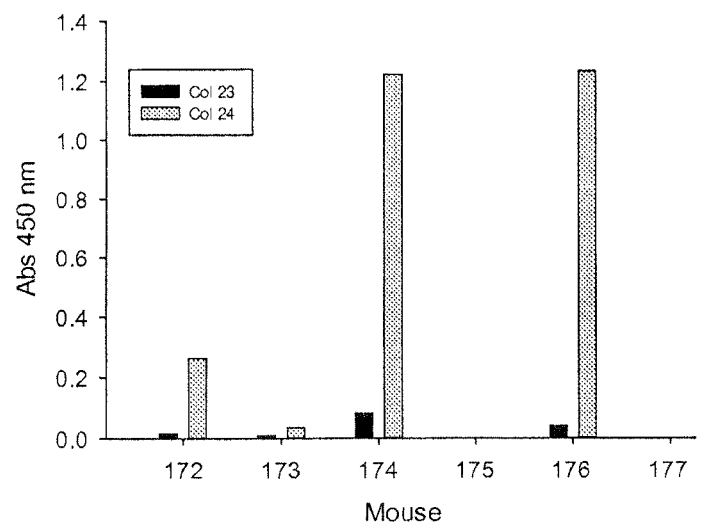
FIG. 39 a)
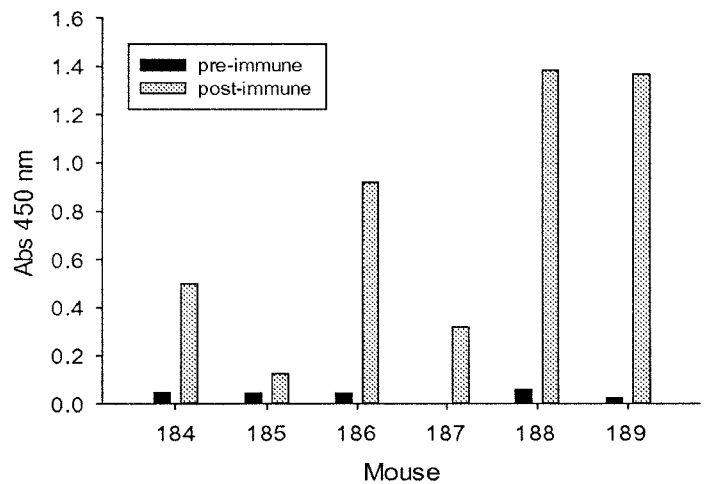
b)
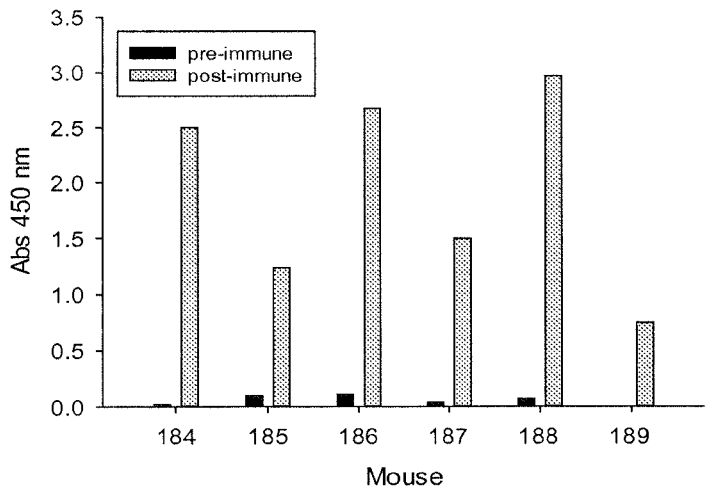
FIG. 41

Immobilized D-Galactose

RECOMBINANT PROTEINS AND THEIR THERAPEUTIC USES

CROSS-REFERENCE TO RELATED APPLICATIONS

This application claims priority from U.S. Patent Application Ser. No. 61/563,128 filed Nov. 23, 2011 entitled "IMMUNOGENIC SYNTHETIC RECOMBINANT PROTEINS" and U.S. Patent Application Ser. No. 61/654,401 filed Jun. 1, 2012 entitled "IMMUNOGENIC SYNTHETIC RECOMBINANT PROTEINS", both of which are incorporated by reference herein in their entirety.

FIELD

The present disclosure relates to the field of recombinant proteins for use in treating diseases.

BACKGROUND

Cancer immunology is the study of interactions between an immune system and cancer cells such as, tumors or malignancies. The initiation of an immune response, such as recognition of cancer-specific antigens, which are expressed by human tumors and not in normal tissues, is of particular interest. Generally, methods to control the division and proliferation of the malignant cells have been to isolate these antigens and present them so that they are recognized by the immune system as non-self antigens and induce a specific immune response.

There are a significant number of growth factors identified at present, and most, if not all, have been shown to be important mediators of cell proliferation in various cancers in addition to being implicated in other disease conditions. Generally, growth factors are soluble serum proteins that recognize, and are bound by a group of growth factor receptors located on cell surfaces. Particular growth factors may be specific for a single receptor, or may bind to more than one closely related receptor with varying affinities. Similarly, some receptors bind only a single growth factor ligand while others can bind to multiple related growth factors, again usually with differing affinities. Upon binding to its natural receptor, the cytoplasmic domain of the receptor is phosphorylated, and this initiates an intra-cellular signaling cascade which results in modulation of transcription of one or more genes and ultimately to progression through the cell cycle and cell proliferation.

Growth factors and their receptors are essential components of the normal processes of growth, development and repair, and their tissue distribution profiles and expression levels closely regulate cell growth. Numerous studies have shown that growth factors can stimulate proliferation of a variety of cell types both in vitro and in vivo (Cohen S., Carpenter G., PNAS USA 72, 1317, 1975, Witsch E et al: Physiology: 25(2):85-101, (2010)). Moreover, certain growth factors have been shown to stimulate proliferation in some cancer cell lines, for example epidermal growth factor (EGF) can stimulate some non-small cell lung carcinoma cells (Osborne C. K. et al. Can Res. 40, 2. 361 (1980)). Other growth factors such as vascular endothelial growth factor (VEGF), fibroblast growth factor (FGF), and platelet-derived growth factor (PDGF) are important in several oncology diseases, such as non-small cell lung cancer (NSCLC) (Ballas M S, Chachoua A., Onco Targets and Therapy: 4, 43-58 (2011)), Prostate cancer, (Cox M E et al; Prostate 69 (1):33-40 (2009)), and Breast cancer (Law J et al, Cancer Res; 68,24:10238-10346 (2008)).

High levels of various growth factor receptors have been reported in malignant tissues. For example, the epidermal growth factor receptor (EGFR) has been detected at unusually high levels in malignant tumors of epithelial origin, such as lung, breast, bladder, ovarian, vulva, colonic, pulmonary, brain and oesophagus cancers. The role played by growth factors and their receptors in regulating tumor growth is unknown, but there are suggestions that growth factor receptor expression in tumor cells provides a mechanism for autocrine growth stimulation which leads to uncontrolled proliferation (Schlessinger J., Schreiber A. B., Levi A., Liberman T., Yarden Y. Crit. Rev. Biochem. 1983, 14 (2) 93-111). Further, Liao Y et al; Hum Pathol 36(11):1186-1196 (2005) and Cox M E et al; Prostate: 69(1) 33-40 (2009) describe the role of increased Insular receptor and growth factor on metastatic prostate cancer.

One treatment strategy to target growth factor signaling in cancer therapy has been to use a passive immunotherapy, such as using monoclonal antibodies against the particular receptor/receptors involved. Such studies have demonstrated that the specific recognition by an antibody of the receptor that is able to inhibit the binding of the ligand can have an inhibitory effect on the mitogenic stimulation of malignant cells (SATO J. D., et al. Methods in Enzymology, vol. 146 pp 63-81, 1987). However, antibodies which are of murine origin will usually produce a human anti-mouse antibody response (HAMA), thus limiting them to a single administration.

Other treatment strategies have been to use an active immunotherapy with vaccines that contain the growth factor of interest to induce an immune response against the molecule to inhibit the proliferation effect of the growth factor on tumors. U.S. Pat. No. 5,984,018, to Davila et al., entitled Vaccine Composition Comprising Autologous Epidermal Growth Factor or a Fragment or a Derivative Thereof having Anti-tumor Activity and use Thereof in the Therapy of Malignant Diseases, discloses, for example, the use of a vaccine that contains a mixture of a growth factor and an immunogenic (i.e. non-human) carrier protein chemically conjugated together using gluterhaldehyde. However, without being bound to any particular theory it is thought that chemical conjugation hinders immune responses against the vaccine.

This is a technically challenging approach, as it requires that the host generates an immune response to a 'self antigen', and vertebrate immune systems have evolved to prevent such responses occurring. Where a strong immune response is generated against a self antigen, for example, one that includes T-helper cell activation, an auto-immune disease state usually results. For many years it has been hypothesized that some auto-immune disorders, for example, lupus, multiple sclerosis (MS), diabetes etc., might be caused by early exposure to an environmental agent that includes immunogenic epitopes (T-cell epitopes) that closely mimic host self-epitopes. This could lead to the stimulation of T-helper cells that are cross reactive with host epitopes. Subsequent exposure to the environmental agent could then result in an anti-self immune response (Albert, L. J., and Inman, R.D New England Journal of Medicine, December 30$^{th}$ pp 2068-2074, 1999). It has since been demonstrated that a viral antigen can indeed generate an anti-self immune response against a nerve cell protein (Levin, M. C. et. al., Nature Medicine vol 8 (5) pp 509-513, 2002).

U.S. Publ. No. 2006/0251654, to Casimiro et al., entitled Method for Treatment of Malignant and Infectious Chronic Diseases, (the '654 publication) discloses a method of treating a subject bearing a malignant or infectious chronic disease comprising the method of immunizing the subject with a vaccine containing a self antigen associated with the malignant or infectious chronic disease that is coupled to a carrier protein; treating the subject with an immune modulator agent; and immunizing the subject again with the vaccine of the step 1, and an appropriate adjuvant selected from aluminum hydroxide and Montanide ISA 51 (Seppic, Paris, France). Unfortunately, the preparation of the vaccine by chemical conjugation is thought to hinder the immune response.

The majority of the vaccines described above exhibit a number of limitations, arising primarily from the method of manufacture and the potential lack of uniformity and homology of the protein product. The vaccines described above generally comprise a mixture of a recombinant carrier protein and polypeptides of human origin that are chemically conjugated using gluterhaldehyde. Unfortunately, this reactive reagent can undesirably form covalent cross-linking bonds between varieties of chemical groups, and generally leads to a highly heterogeneous product. Thus, the resulting vaccines may comprise not only carrier protein molecules with varying numbers of the target human polypeptide attached (for example, 0, 1, 2, 3 etc.), but the human polypeptides can each be attached to the carrier via different atoms and so in different positions and in different orientations. Furthermore, both the target polypeptide and carrier protein molecules may be conjugated to themselves, resulting in various homo-multimers that may have no clinical efficacy and may not contribute to an anti-cancer patient immune response.

SUMMARY

The present disclosure is directed towards recombinant proteins and their respective methods of manufacturing; the characterization of the recombinant proteins and therapeutic methods of using the recombinant proteins to treat chronic diseases, such as, for example, lung, breast, bladder, prostate, ovarian, vulva, colonic, colorectal, intestinal, pulmonary, brain, esophageal, other cancers, and other diseases.

In an illustrative embodiment, the recombinant protein is an immunogenic protein molecule expressing one or more sequences that fold into a physical structure, for example expressing one or more sequences of a cholera toxin B (CT-B) protein from *Vibrio cholera* or a synthetic equivalent, and expressing one or more sequences of one or more epitopes from human growth factors. The expressions of the growth factors or parts thereof can be present at multiple sites, as a single antigen, in tandem, and/or longer chains of antigen molecule(s) per site.

In another illustrative embodiment, the recombinant protein is an immunogenic protein molecule expressing one or more sequences that fold into a physical structure, for example expressing one or more sequences of a cholera toxin B (CT-B) protein from *Vibrio cholera* or a synthetic equivalent, and expressing one or more sequences of one or more tumor antigens or parts thereof. The recombinant protein may also include one or more sequences of one or more growth factors or parts thereof, and/or one or more sequences of one or more receptors or parts thereof.

In another illustrative embodiment, the recombinant protein is an immunogenic protein molecule expressing one or more sequences that fold into a physical structure, for example expressing one or more sequences of a cholera toxin B (CT-B) protein from *Vibrio cholera* or a synthetic equivalent, and expressing one or more sequences of one or more receptors or parts thereof. The recombinant protein may also include one or more sequences of one or more growth factors or parts thereof, and/or one or more sequences of one or more tumor antigens or parts thereof.

In these illustrative embodiments, the expressions of the tumor antigen(s) or parts thereof, the receptor(s) or parts thereof, and/or the growth factor(s) or parts thereof can be present at multiple sites, as a single antigen or receptor, in tandem, and/or longer chains of antigen or receptor molecule(s) per site.

In an illustrative embodiment, the sequence of the tumor antigen may include a sequence of a Prostate Specific Antigen (PSA) or part thereof. In an illustrative embodiment, the sequence of the receptor may include a sequence of a Human Epidermal Growth Factor Receptor 2 (Her2) or part thereof and/or a Human Epidermal Growth Factor Receptor 3 (Her3) or part thereof.

In an illustrative embodiment, the sequence of the growth factor may include a sequence of an epidermal growth factor (EGF) or a substantial portion of the appropriate coding region(s) of the EGF including a neutralizing domain of the EGF at one or more positions within the recombinant protein. In other illustrative embodiments, the sequence of the growth factor may include a full length or part thereof of one or more of the following growth factors, and/or alternative self-antigens such as, but not limited to, other growth factors, including, but not limited to, EGF, IGF-1, IGF-2, FGF, TGF-β, TGF-α, VEGF-A, VEGF-B, VEGF-C, VEGF-D, PDGF, NGF, EGF, HGF, BMP's, and IL's 1-6. It is contemplated within the scope of the disclosure that growth factors may be selected from human and non-human origins. It is further contemplated within the scope of the disclosure that said sequence of growth factors can substantially similar to either human or non-human growth factors or said sequence can contain functional parts thereof. Further, the recombinant protein may include one or more expressions of other sequences that can be used to functionally model part or all of the growth factors within a recombinant immunogenic protein sequence. In one embodiment, additional flanking residues may also be expressed or added to the minimum sequence to allow the entire neutralizing domain of the molecule to be presented in a natural conformation and to be accessible to cells of the immune system.

In the context of the present disclosure, "neutralizing domain" is defined as a region or regions of either or both member(s) of a specific binding pair, e.g. a growth factor and its cognate receptor, wherein the binding of a third molecule that is not a member of the specific binding pair to the aforementioned region(s) will prevent the subsequent binding of the two members of the specific binding pair. The third molecule can be another protein molecule including but not limited to an antibody, or can be a small non-protein molecule, and can be either natural or synthetic in origin. The neutralizing domain will normally include those regions of the members of the specific binding pair that are in direct contact during binding, and will also include regions outwith said regions where upon binding of a third molecule introduces sufficient stearic hindrance to prevent the members of the specific binding pair from binding directly.

It is well established in the field that specific recognition of a ligand by its cognate receptor is defined by an interaction between the binding site of the receptor and a particular molecular signature (epitope) of the ligand. Thus an antibody that either binds to or otherwise blocks the receptor binding site, or binds to or otherwise blocks the recognition epitope of the ligand, will prevent ligand-receptor interactions. Such antibodies are described as being "neutralizing." In the context of the present disclosure it is desirable that neutralizing antibodies are generated by the host upon administration of the recombinant protein, and thus the protein sequence may express or include one or more of all of, or a suitable sequence derived from, a growth factor or tumor antigen such that epitopes required for receptor binding are presented in a functional (native) conformation.

In addition to expressing multiple copies of a single tumor antigen, receptor, and/or growth factor, presented as a single tumor antigen, receptor, and/or growth factor or part thereof per physical site, and/or as chains of repetitive tumor antigen, receptor, and/or growth factor sequences (for example, n=1 or more); the protein according to the disclosure may also include expressions of one or more epitopes or binding sites from two or more different tumor antigens, receptors, and/or growth factors present as single or as chains at different positions within the sequence of the recombinant protein.

The resulting protein may be a single polypeptide expressing a tumor antigen, a receptor, and/or a growth factor or one or more epitopes or binding sites thereof within the sequence of the recombinant protein. In an illustrative embodiment, the sequence of the recombinant protein expresses one or more portions of a CT-B sequence and presents the tumor antigen, receptor, and/or growth factor expression(s) or one or more expression(s) of epitopes or binding sites thereof on a surface of the recombinant protein in a natural conformation.

In another illustrative embodiment, a process of preparing a protein formulation is disclosed. In this illustrative embodiment, the process includes assembling one or more single monovalent or multivalent monomers together preparing a multivalent vaccine including a recombinant protein including one or more tumor antigens, receptors, and/or a growth factors or parts thereof.

In yet another illustrative embodiment, a process for treating a patient is disclosed. In this illustrative embodiment, the process includes administering separately to the patient one or more monovalent or multivalent, one tumor antigen, receptor, and/or growth factor, synthetic proteins in a same day or at alternate days or times during a vaccination period.

In a further illustrative embodiment, a process for treating a patient is disclosed. In this illustrative embodiment, the process includes administering separately to the patient one or more monovalent or multivalent vaccine, one tumor antigen, receptor, and/or growth factor, synthetic proteins in a pharmaceutically acceptable carrier including an adjuvant to promote an immune response.

BRIEF DESCRIPTION OF THE DRAWINGS

The embodiments described in the present disclosure are illustrated in the figures of the accompanying drawings which are meant to be exemplary and not limiting, in which like references are intended to refer to like or corresponding parts, and in which:

FIG. 1 illustrates a table of sequences and structures of EGF molecules from a range of organisms;

FIG. 9 illustrates a line graph of the binding of anti-EGF neutralizing domain mAb 10827 to 6 EGF-CT-B synthetic proteins captured by a rabbit anti-CT-B antibody;

FIG. 10 illustrates a Western blot of the 6 monovalent synthetic EGF-CT-B proteins run on SDS gel under native (non-boiled) conditions, and detected with an anti-CT-B antibody;

FIG. 11 illustrates a line graph of the binding of anti-EGF neutralizing domain mAb 10827 to synthetic EGF-CT-B proteins including either 2 full length EGF sequences (E2) or two partial EGF sequences (B2);

FIG. 12 illustrates a Western blot of the bivalent synthetic EGF-CT-B proteins run on non-denaturing SDS-PAGE gels;

FIG. 13 illustrates a synthetic protein sequence including two full length EGF sequences (underlined) and a CT-B sequence (italics);

FIG. 14 illustrates a synthetic protein sequence including two EGF neutralizing domain sequences (underlined) and the CT-B sequence (italics);

FIG. 15 illustrates a synthetic protein sequence including two partial sequences of the EGF molecule including the EGF neutralizing domain, Cys6 to Cys31, (underlined) and the CT-B sequence (italics);

FIG. 16 illustrates a Western blot showing the effect of pH shift on the multimerisation of native CT-B protein. Samples on the right side of the gel were incubated for 5 min at the pH indicated below prior to gel analysis. Samples on the left side were incubated at the pH indicated below for 5 min., then neutralized back to pH 7.0 for 1 hour prior to gel analysis;

FIG. 17 illustrates a table of constructs T1-T6, E2, and B2 including sequences expressing EGF and CT-B;

FIG. 18 illustrates a Western blot of the E2 and B2 constructs;

FIG. 19 illustrates constructs E2, E2N, and E2C including sequences expressing EGF and CT-B;

FIG. 20 illustrates constructs including sequences expressing EGF and CT-B and containing extended amino acid linkers;

FIG. 21 illustrates a Western blot of the E2, E2N, and E2C constructs;

FIG. 22 illustrates a Western blot of a number of N-terminus constructs including the extended amino acid linkers; and FIG. 23 illustrates a Western blot of a number of C-terminus constructs including the extended amino acid linkers.

FIG. 24 illustrates a synthetic protein sequence including IGF1 (Underlined), EGF (underlined and italics) and the CT-B sequences (italics);

Figure 27:
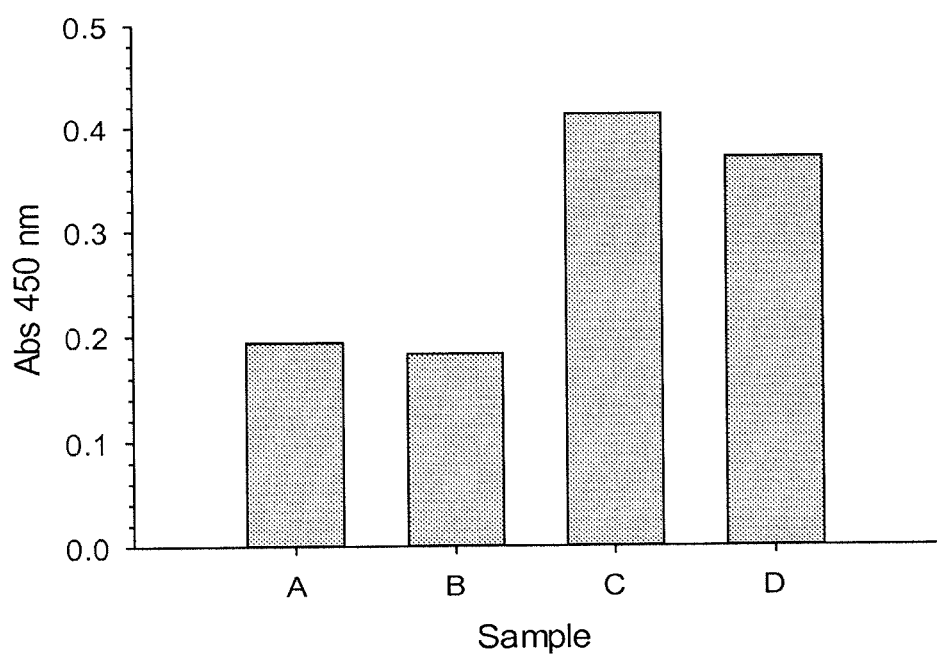
Figure 29:
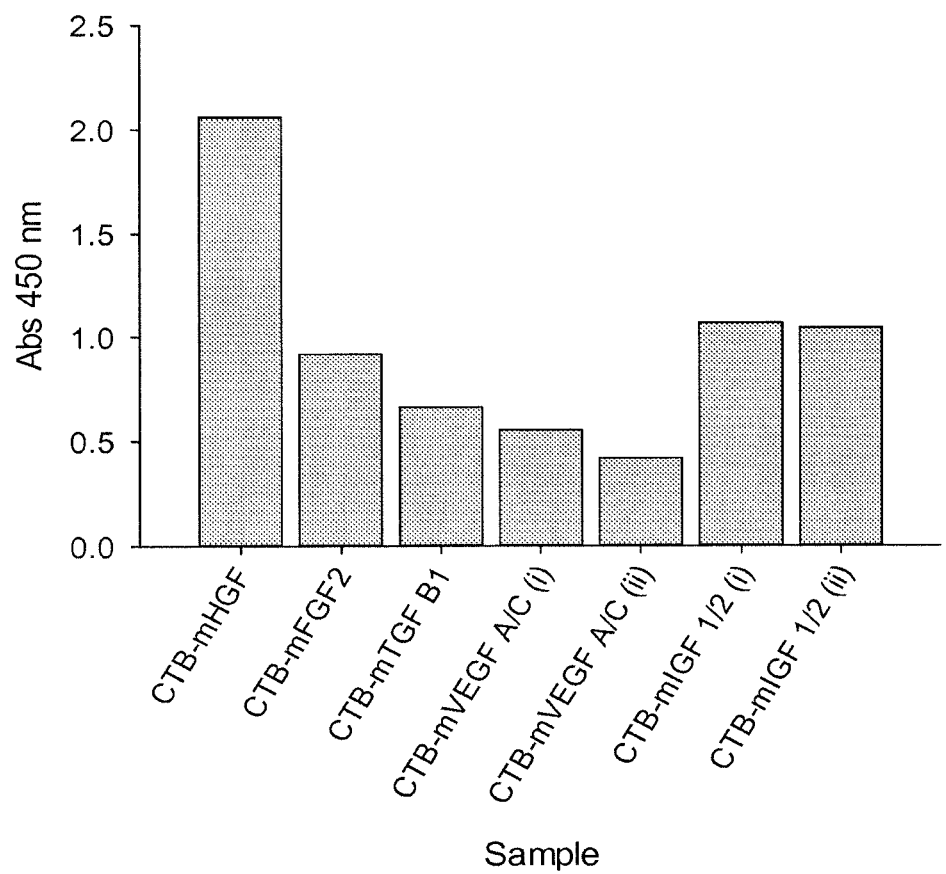
Figure 30:
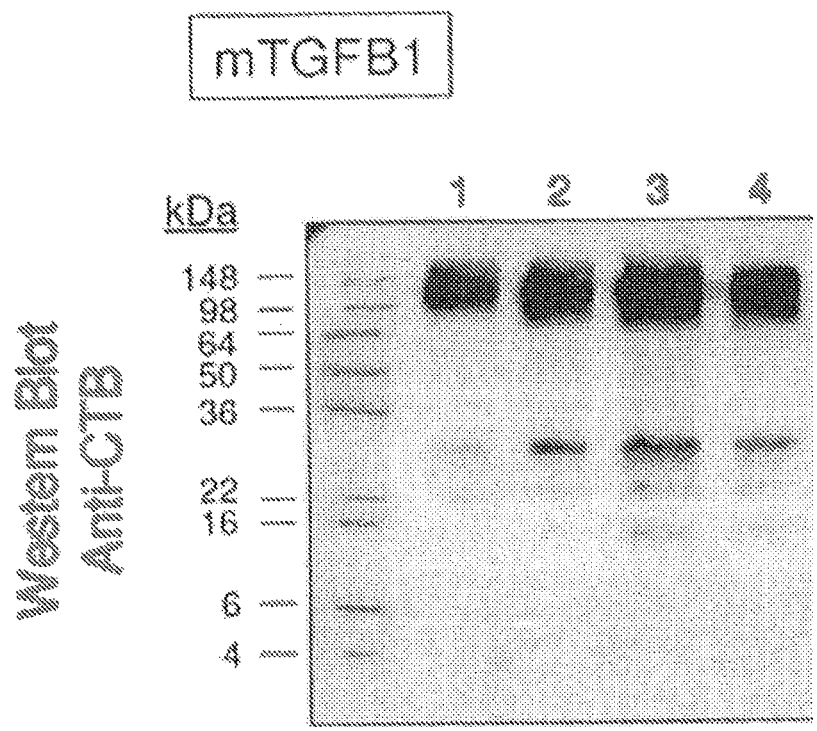
Figure 32:
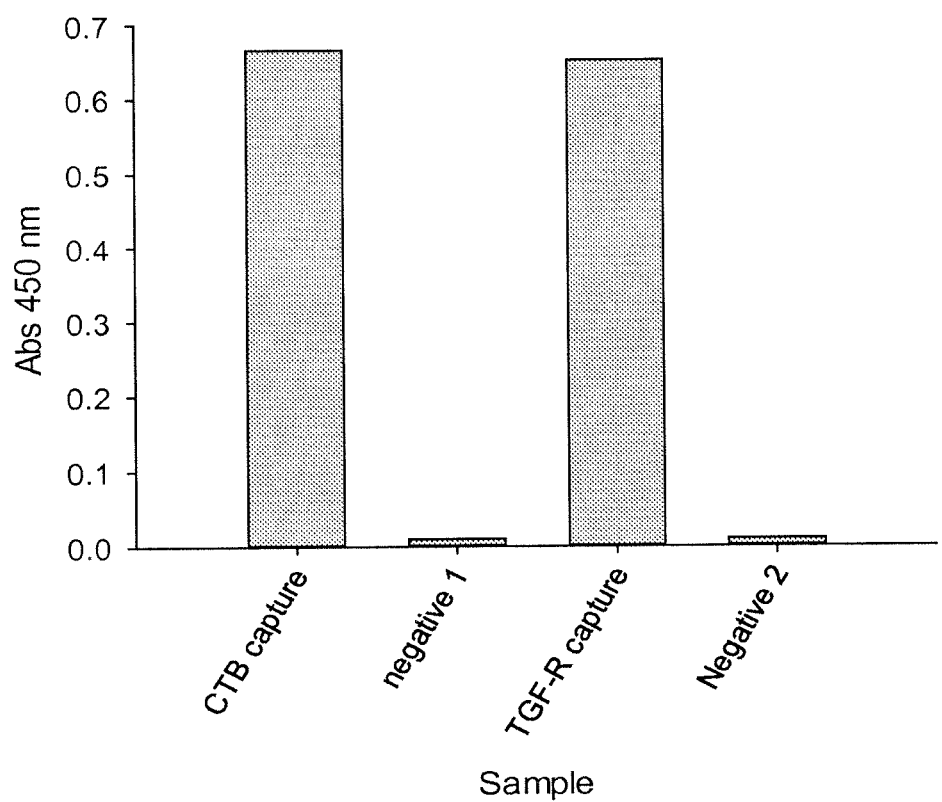
Figure 33:
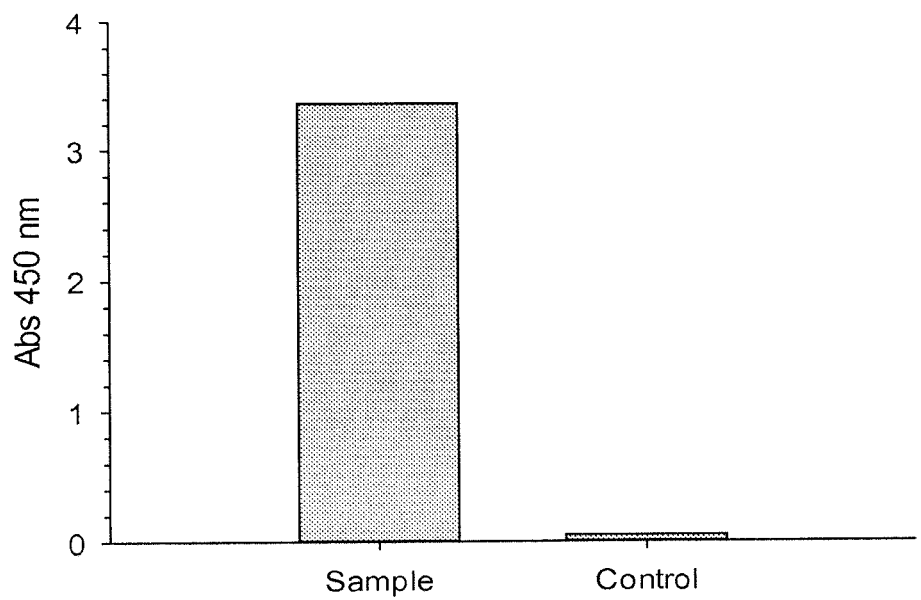
Figure 34:
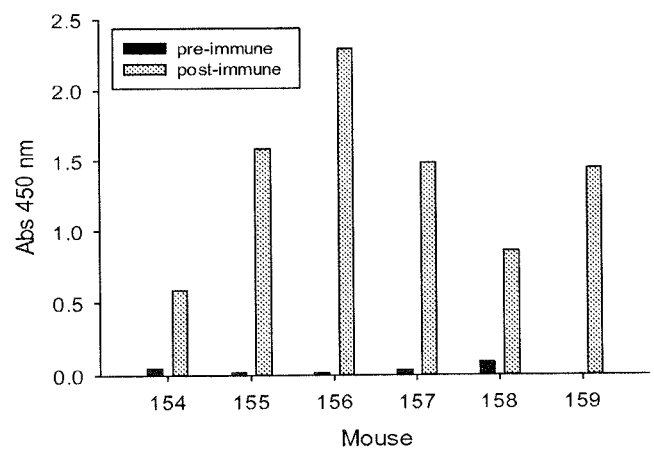
Figure 35:
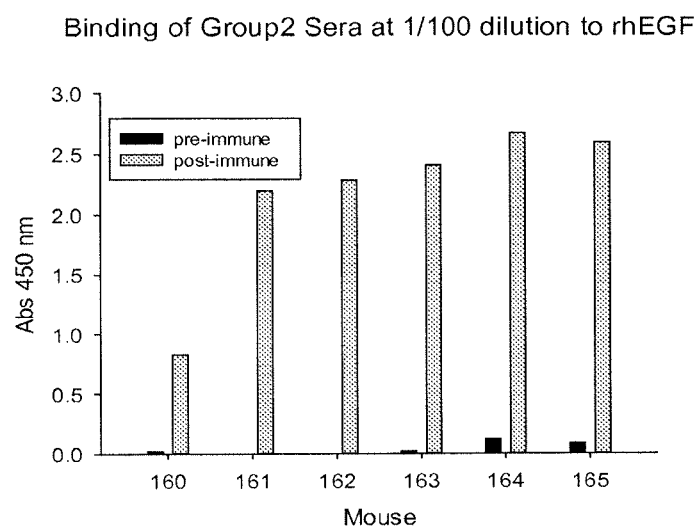
Figure 40:
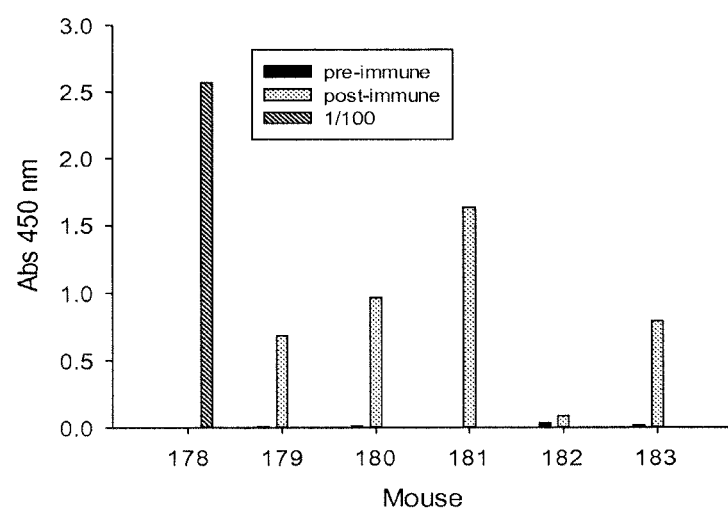
Figure 42:
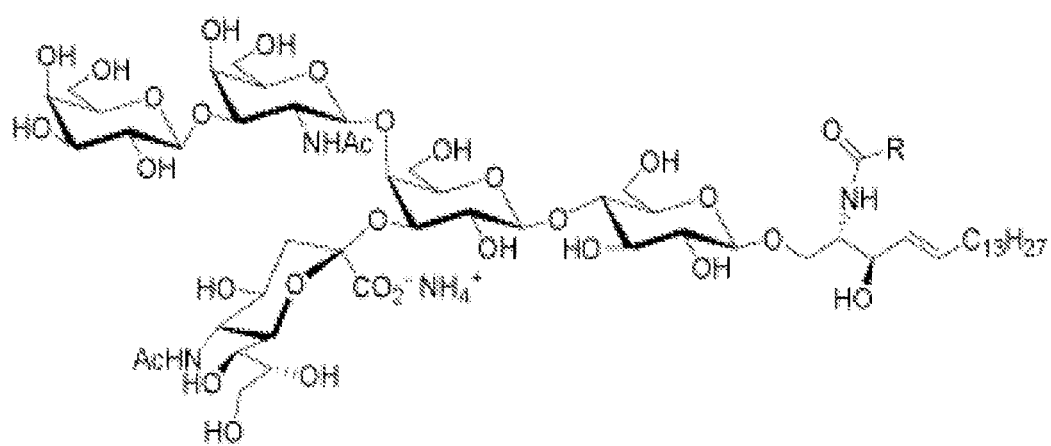
Figure 43:
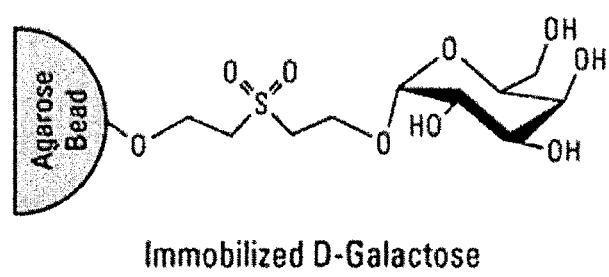
Figure 44:
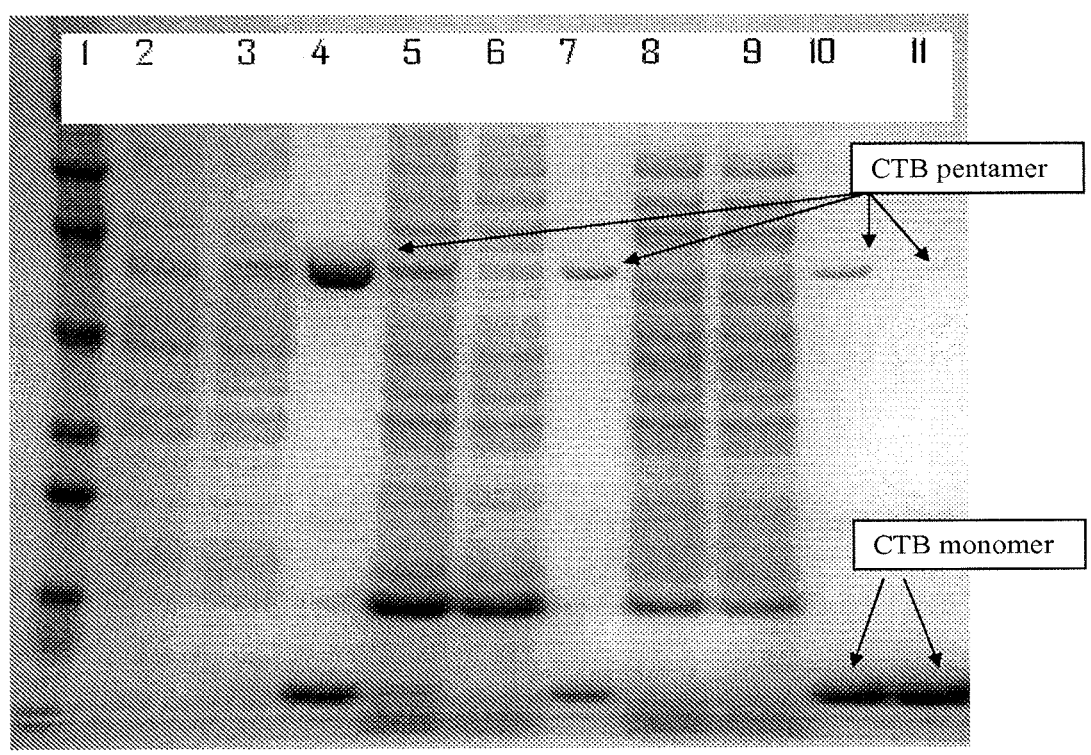

FIG. 25 illustrates a bar graph of a capture ELISA demonstrating the simultaneous presence of IGF, EGF and CTB sequences on a single recombinant protein. Bars A and B were captured by anti-EGF antibody, and bar C by anti-IGF antibody. Proteins were detected as follows: A anti-CTB, B anti-IGF and C anti-CTB;

FIG. 26 illustrates a synthetic protein sequence including Hu-IGF1 sequence (underlined) and the CT-B sequence (italics);

FIG. 27 illustrates a bar graph of a capture ELISA in which hetero-oligomers of IGF-CTB and EGF-CTB are detected. All samples include IGF C-terminal to CTB. Samples A and B include EGF C-terminal to CTB, and samples B and D include EGF N-terminal to CTB. Samples A and B were captured with an anti-EGF antibody, and IGF was detected, whereas samples C and D were captured with an anti-IGF antibody and EGF was detected;

FIG. 28 (a-e) illustrates synthetic protein sequences including CT-B sequence (italics) and the growth factor sequences (underlined) of a) TGF-Beta1, b) FGF2, c) HGF (NK1), d) IGF1/2 and e) VEGF-A/C (VEGF-C sequence underlined and in italics);

FIG. 29 illustrates a bar graph of a capture ELISA of a diverse range of chimeric recombinant proteins including sequences derived from one or more growth factors together with CTB sequences. In each case, recombinant protein was captured by an antibody specific for one of the sequences and then detected with a antibody specific for a different sequence as follows:

HGF and TGF B1 were captured with α-HGF and α-TGF B1 antibodies, and CTB was detected;

FGF2 was captured with α-CTB antibody and FGF2 detected;

VEGF A/C was captured with (i) α-VEGF-A antibody and (ii) α-VEGF-C antibody, and CTB was detected in both cases;

IGF1/2 was captured by α-IGF1 antibody in both cases, and detected with (i) α-CTB antibody and (ii) α-IGF2 antibody;

FIG. 30 illustrates a Western blot of a SDS-PAGE gel of native recombinant TGF B1-CTB protein according to FIG. 28a demonstrating the presence of primarily pentameric recombinant protein;

FIG. 31 illustrates a synthetic protein sequence including a) a synthetic protein sequence including TGF-B1 sequence (underlined) and the CT-B sequence (italics) and b) TGF-Beta2 receptor ligand binding domain sequence (underlined) and the CT-B sequence (italics);

FIG. 32 illustrates a bar chart of a capture ELISA of the recombinant protein containing both TGF-Beta-R2 and CTB sequences. The graph demonstrates that both sequences can be bound simultaneously in both orientation without bias;

FIG. 33 illustrates that recombinant protein containing sequences derived from TGF-beta and CTB is able to bind to recombinant protein containing sequences derived from the ligand binding domain of TGF beta receptor 2 and CTB;

FIG. 34 illustrates the IgG antibody responses of Group 1 mice sera at 1/100 dilution to r-IGF following immunization;

FIG. 35 illustrates the IgG antibody responses of Group 2 mice sera at 1/100 dilution to r-EGF following immunization;

FIG. 36 illustrates the IgG antibody responses of Group 3 mice sera at (a) 1/100 dilution and (b) 1/8 dilution to r-EGF following immunization;

FIG. 37 illustrates the IgG antibody responses of Group 3 mice sera at (a) 1/100 and (b) 1/8 dilution to r-IGF following immunization;

FIG. 38 illustrates the IgG antibody responses of Group 4 mice sera at (a) 1/100 and (b) 1/8 dilution to r-EGF following immunization;

FIG. 39 illustrates the IgG antibody responses of Group 4 mice sera at (a) 1/100 and (b) 1/8 dilution to r-IGF following immunization;

FIG. 40 illustrates the IgG antibody responses of Group 5 mice sera at 1/8 dilution (except sample 178 at 1/100) to r-IGF following immunization;

FIG. 41 illustrates the IgG antibody responses of Group 6 mice sera at 1/100 dilution to a) r-IGF and b) rHu-EGF following immunization;

FIG. 42 illustrates the structure of mono-ganglioside GM1, the natural binding partner of cholera toxin sub-unit B;

FIG. 43 illustrates the structure of commercially available D-galactose conjugated to a solid support (Pierce); and FIG. 44 illustrates a SDS-PAGE gel of the purification of rCTB from the culture supernatant (media) of three strains of *E. coli* cells transformed with a CTB expression vector as follows: Lane 1 show size marker. Lanes 2, 5 and 8 show crude culture supernatant. Lanes 3, 6 and 9 show crude periplasmic fractions. Lanes 4, 7 and 10 show eluted purified CTB. Lane 11 shows His-tagged CTB purified by IMAC.

DETAILED DESCRIPTION

Detailed embodiments of the present recombinant proteins or vaccines are disclosed herein, however, it is to be understood that the disclosed embodiments are merely exemplary, which may be embodied in various forms. Therefore, specific functional details disclosed herein are not to be interpreted as limiting, but merely as a basis for the claims and as a representative basis for teaching one skilled in the art to variously employ the recombinant protein disclosed herein.

The present disclosure provides a homogeneous recombinant protein for improving the presentation of the maximum number of growth factor epitopes, tumor antigen epitopes, and/or receptor binding sites as elements of an immunogenic recombinant protein. In one illustrative embodiment, a recombinant protein expressing all or portions of a cholera toxin B (CT-B), and a human epidermal growth factor (EGF), a tumor antigen, and/or a receptor is described. In alternative illustrative embodiments, the protein may express other immunogenic recombinant proteins that are modeled based upon known immunogenic proteins. It is contemplated within the scope of the disclosure that such recombinant proteins will be expressions of polypeptides that are highly immunogenic to the human immune system. Preferably, the recombinant proteins confer additional properties to the chimeric protein, for example, high expression yield and ease of manufacture, oral stability and the ability to cross from gut to blood stream, and/or previous safe use in humans.

In an illustrative embodiment, the recombinant proteins disclosed herein may include or express a high proportion of a protein sequence derived from target self antigens, as a function of total molecular weight. This can be achieved, for example, by using a large protein model containing multiple growth factor epitopes. These growth factor epitopes can be multiple copies of whole or part of a single growth factor, or copies of whole or part of more than one different growth factor.

Figure 2:
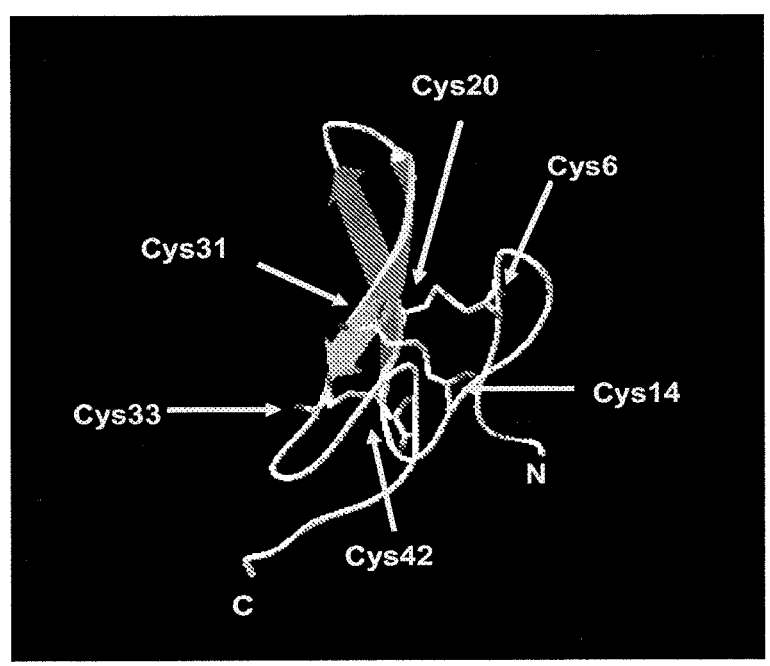
FIG. 2 illustrates an embodiment of a structure of a human EGF molecule, including an EGF neutralizing domain.
Figure 3:
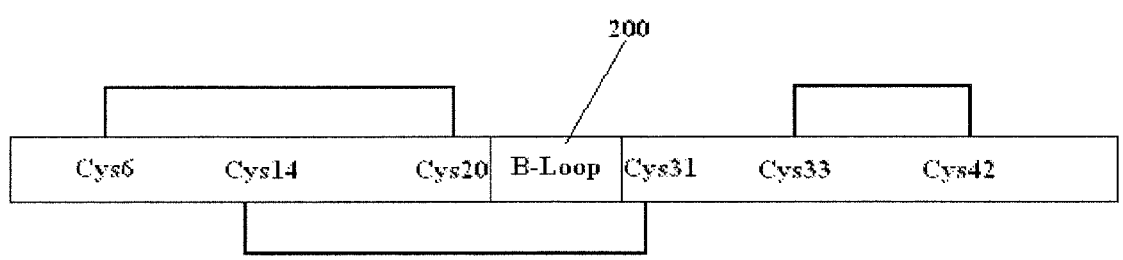
FIG. 3 illustrates an embodiment of a simplified line structure of the EGF molecule's cysteine pairs, including the EGF neutralizing domain.
Figure 4:
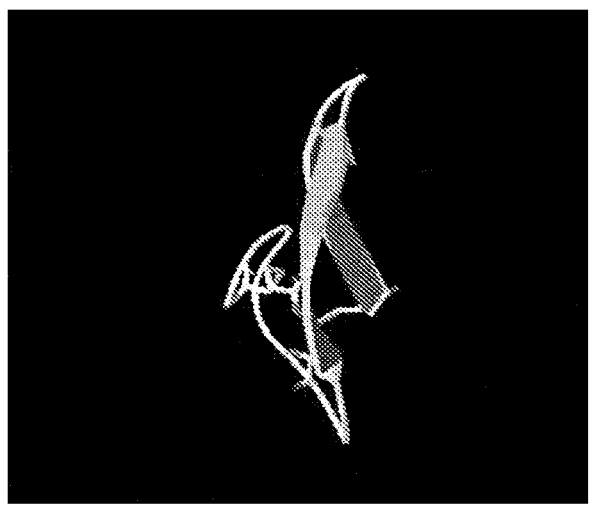
FIG. 4 illustrates an embodiment of a minimum sequence of the EGF molecule that presents the EGF neutralizing domain in a correct conformation.

According to the disclosure, the expressions of the growth factor epitopes should be folded allowing their natural conformation to be substantially retained and presented to components of the host immune system in such a way as to elicit a robust host immune response to said epitopes. Examples of suitable natural protein models to model an epitope supporting domain of a recombinant protein include, but are not limited to, cholera toxin B sub-unit, *E. coli* heat-labile LT and LT-II enterotoxin B subunits, veratoxin, pertussis toxin, *C. jejuni* enterotoxin, Shiga toxin, listeria toxin, tetanus toxoid, diphtheria toxoid, *N. meningitidis* I outer membrane protein, bacteriophage coat protein, adenovirus and other viral coat proteins. Alternatively, a non-self component of the protein can be small. As a minimum, the non-self sequence(s) should comprise about 9, 10, 11 or more amino acids in length, and include either entirely or in-part at least one human T-cell epitope. Alternatively, non-natural 'synthetic' polypeptides may be used that fulfill the requirements of conferring immunogenicity to the whole protein and allowing appropriate presentation of growth factor(s), receptors, tumor antigens or epitopes thereof to the host immune system.

In an illustrative embodiment, the epitope supporting domain of the recombinant protein, whether derived from a natural or synthetic polypeptide sequence, should have the capacity to self-assemble into oligomeric multimers under appropriate chemical/environmental conditions, or to be reduced to monomers under alternative conditions. Ideally, multimerisation domains will assemble into stable multimers with a discreet number of sub-units, for example dimers, trimers, tetramers, pentamers, etc., such that a product of homogeneous size is generated. Examples of natural polypeptides include, but are not limited to, leucine zippers, lac repressor protein, streptavidin/avidin, cholera toxin B subunit, B sub-units of other $AB_5$ toxins, *Pseudomonas* trimerization domain, and viral capsid proteins.

According to the disclosure the recombinant proteins, whether either growth factors or parts thereof, cellular receptors or parts thereof, tumor antigens or parts thereof, are related to broad range of either cellular pathways involved in chronic disease or cancers for growth factors and receptors and to broadest possible range of solid tumors for use of tumor antigens within the said synthetic proteins. The proteins are in the form of a recombinant protein and may be useful in treating chronic diseases, for example, breast, lung, bladder, ovarian, vulva, colonic, pulmonary, brain, colorectal, intestinal, head and neck, and esophagus cancers. As different tumor antigens can be expressed and multiple cellular receptors and growth factors over expressed in the said diseases, the proteins described hereunder can contain one or more different tumor antigens, one or more different receptors or growth factors of one or multiple cellular pathways associated with the disease. These proteins are called" multivalent."

In an illustrative embodiment, a protein comprised of a homogeneous recombinant protein expressing one or more epidermal growth factor (EGF) neutralizing domains is disclosed. The protein is in the form of a recombinant protein and may be useful in treating chronic diseases, for example, breast, lung, bladder, ovarian, vulva, colonic, pulmonary, brain, colorectal, head and neck, and esophagus cancers. In an illustrative embodiment, the protein is a recombinant protein expressing or including EGF sequences and CT-B sequences.

In another illustrative embodiment, a protein comprised of a homogeneous recombinant protein expressing one fibroblast growth factor (FGF) is disclosed. In an illustrative embodiment, the protein is a recombinant protein expressing or including FGF sequences and CT-B sequences.

In a further illustrative embodiment, a protein comprised of a homogeneous recombinant protein expressing one transforming growth factor-Beta 1 (TGF-β1) is disclosed. In an illustrative embodiment, the protein is a recombinant protein expressing or including TGF-β1 sequences and CT-B sequences.

In yet another illustrative embodiment, a protein comprised of a homogeneous recombinant protein expressing one transforming growth factor-Beta 1 (TGF-β1) is disclosed. In an illustrative embodiment, the protein is a recombinant protein expressing or including TGF-β1 sequences and CT-B sequences.

In one illustrative embodiment, a protein comprised of a homogeneous recombinant protein expressing one insulin-like growth factor-1 (IGF-1) is disclosed. In an illustrative embodiment, the protein is a recombinant protein expressing or including IGF-1 sequences and CT-B sequences.

In another illustrative embodiment, a protein comprised of a homogeneous recombinant protein expressing one hepatocyte growth factor (HGF) is disclosed. In an illustrative embodiment, the protein is a recombinant protein expressing or including HGF sequences and CT-B sequences.

In a further illustrative embodiment, a protein comprised of a homogeneous recombinant protein expressing one Insulin-like growth factor-1 (IGF-1) and one insulin-like growth factor-2 is disclosed. In an illustrative embodiment, the protein is a recombinant protein expressing or including IGF-1 sequences, IGF-2 sequences and CT-B sequences.

In yet another illustrative embodiment, a protein comprised of a homogeneous recombinant protein expressing one vascular endothelial growth factor-A (VEGF-A) and one vascular endothelial growth factor-C (VEGF-C) is disclosed. In an illustrative embodiment, the protein is a recombinant protein expressing or including VEGF-A neutralizing domain sequences, VEGF-C sequences and CT-B sequences.

To determine the appropriate coding region(s) of the HuEGF to express or include, the sequences and structures of EGF molecules from a range of organisms are analyzed. A table illustrating sequences and structures of EGF molecules from a range of organisms is described with reference to FIG. 1. As illustrated in FIG. 1, a box 100 encloses a portion of the sequence of the EGF molecules from the range of organisms, which represents the neutralizing domain epitope of the EGF molecules. While there is a significant amount of conservation between the neutralizing domain epitopes of the EGF molecules from different species, there is also a great deal of variation between species. Notably for in vivo studies, one neutralizing domain (boxed sequence 100) is fully conserved amongst primates, but is different in rodents and other species. Similarly, the different sequences of the EGF molecules equate to differences in tertiary structure.

A structure of the human EGF molecule, including the EGF neutralizing domain, according to an illustrative embodiment is described with reference to FIG. 2. The EGF molecule contains six cysteine residues including Cys6, Cys14, Cys20, Cys31, Cys33, and Cys42. The six cysteine residues are important in determining the folding of the EGF molecule. The EGF neutralizing domain 200 (illustrated as an anti-parallel (3-sheet) is constrained by two separate disulphide linked cysteine pairs, Cys6-Cys20 and Cys14-Cys31. The two disulphide linked cysteine pairs, Cys6-Cys20 and Cys14-Cys31 are important because these two pairs define the minimum sequence or minimum peptide of the EGF molecule that presents the EGF neutralizing domain 200 in the correct conformation.

A simplified line structure of the EGF molecule's cysteine pairs, including the EGF B-loop 200, according to an illustrative embodiment is described with reference to FIG. 3. As illustrated in FIG. 3, Cys6 is linked to Cys20, Cys14 is linked to Cys31, and Cys33 is linked to Cys42. The EGF B-loop 200 is located between Cys20 and Cys31. Thus, the minimum sequence or minimum peptide 400 of the EGF molecule that presents the EGF neutralizing domain 200 in the correct conformation is the sequence from Cys6 to Cys31, as illustrated in FIG. 4.

Figure 5:
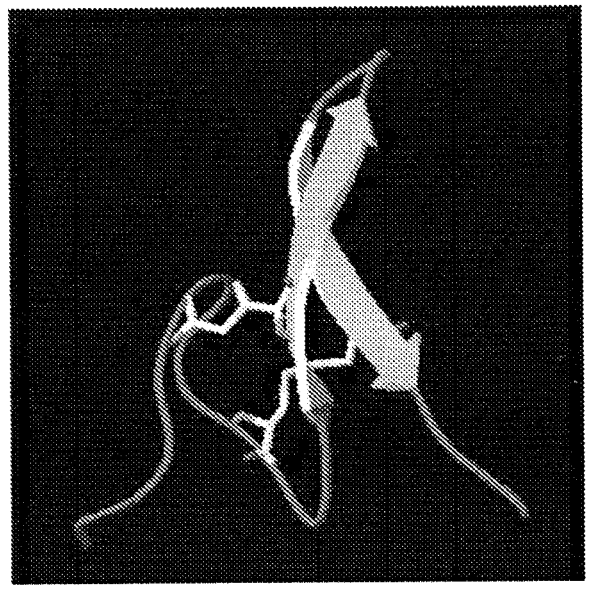
FIG. 5 illustrates an embodiment of a structure of a modified synthetic molecule, expressing the EGF neutralizing domain.

A structure of a modified recombinant protein molecule according to the disclosure expressing at least a portion of the EGF molecule, including the EGF neutralizing domain according to an illustrative embodiment is described with reference to FIG. 5. A single mutation or change is made to Cys33 of the EGF molecule to produce the modified synthetic molecule changing Cys33 to Ala33 to remove the Cys33 to prevent any possible mis-folding problems.

Alanine is used because alanine is fairly 'neutral' in terms of functional characteristics and has the smallest side chain apart from glycine. Alanine is therefore considered the least likely residue to impart any non-native characteristics to the modified recombinant protein. It is contemplated within the scope of the disclosure that potentially any other residue could be used, or even no change made at all.

In an illustrative embodiment, any part of the EGF molecule could be used from the region defined by residues Met21-Ala30 up to the entire EGF sequence. The sequences selected for expression in the recombinant EGF-CT-B proteins in the examples include all of the EGF sequence, and separately a region that is thought required for correct presentation of the neutralizing domain defined as a neutralizing domain in the context used, and doesn't include any other part of the EGF that is not considered necessary to achieve this.

In another illustrative embodiment, a protein comprised of a homogeneous recombinant protein expressing a neutralizing domain of vascular endothelial growth factor-A (VEGF-A) is disclosed. In an illustrative embodiment, the protein is a recombinant protein expressing or including VEGF-A sequences and CT-B sequences. In an illustrative embodiment, the VEGF-A sequence will include the neutralizing domain comprising the sequence from Cys57 to Cys104 of the mature protein. In another illustrative embodiment, the sequence of VEGF-A will include one or more flanking residues extending up to Val14 and Lys108.

In another illustrative embodiment, a protein comprised of a homogeneous recombinant protein expressing the ligand binding domain of TGF-Beta receptor II is disclosed. In an illustrative embodiment, the protein is a recombinant protein expressing or including TGFB-RII sequences and CT-B sequences. The TGFB-RII sequence will include any sequence of the extra-cellular domain between Thr23 and Gln166.

In another illustrative embodiment, a protein comprised of a homogeneous recombinant protein expressing the ligand binding domain of the HGF receptor (c-Met) is disclosed. In an illustrative embodiment, the protein is a recombinant protein expressing or including HGF receptor sequences and CT-B sequences. Preferably, the HGF receptor sequence will include any sequence of the extra-cellular SEMA domain between Lys27 and Leu515.

Example I: ELISA Protocols

In order to determine whether recombinant proteins, such as the synthetic EGF-CT-B proteins according to the disclosure, can display the EGF B-loop in the correct conformation, two commercial monoclonal antibodies (Santa Cruz Antibodies, Cat No's 10825 and 10827) that were known to block binding of EGF to the EGF receptor were obtained. Without being bound to any particular theory, it is postulated from a number of sources that binding to the EGF receptor is achieved in part via the region defined by residues Met21-Ala30.

Figure 6:
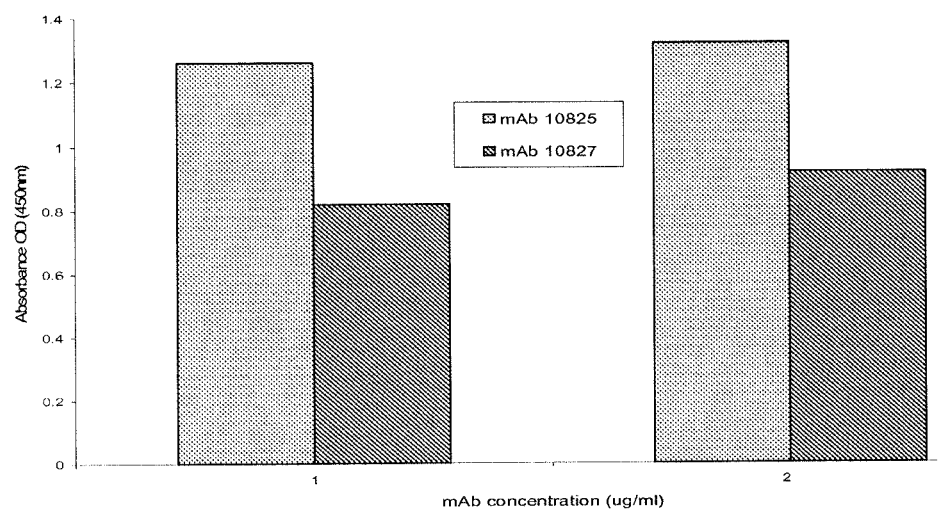
FIG. 6 illustrates a bar graph of mAb 10825 and mAb 10827 binding to rHuEGF with optical density (OD) measured at 450 nm.

In an illustrative embodiment, 1 ug/ml and 2 ug/ml concentrations of mAb 10825 and mAb 10827 were used to bind a recombinant EGF (rEGF) protein in ELISA, and optical density (OD) was measured at 450 nm. The results are illustrated in a bar graph with reference to FIG. 6. As illustrated in FIG. 6, the rEGF retains its natural conformation when adsorbed onto an ELISA plate and 1 ug/ml of either mAb 10825 or mAb 10827 is sufficient to obtain a good signal.

To assess recognition of residues Met21-Ala30, a plate was coated with about 100 ul/well protein (rEGF) at about 1 ug/ml and incubated at about 37° C. for about 1 h. The plate was washed twice with about 200 ul/well PBS-0.5% Tween (PBST), then twice with about 200 ul PBS. The plate was blocked with about 200 ul/well PBS-2% milk powder (MPBS) and incubated for about 1 hour at about 37° C. The plate was then washed twice with PBST and twice with PBS, as above. About 100 ul of the test antibodies were added at either about 1 ug/ml or about 2 ug/ml and incubated for about 1 hour at about room temp (RT). The plate was washed again as described above. Secondary, an antibody (HRP-labeled anti-mouse Fc-specific, Sigma product code A0168) was added at about 1/1000 dilution, about 100 ul/well and incubated for about 1 h at about RT. The plate was washed again as above, and developed with about 100 ul/well Sureblue TMB substrate until color developed (usually about 5-10 min). The reaction was stopped with about 50 ul/well 1M H2SO4, and the plate was read at about 450 nm.

Additionally, a competitive binding ELISA was carried out. In the second ELISA the binding of each of the mAb 10825 and mAb 10827 antibodies to rEGF was assessed in the presence of either free soluble peptide corresponding to the epitope of interest (peptide sequence MYIEALDKYA) or a control irrelevant peptide (peptide sequence SLAGSSGALSK). ELISAs with about 100 ul/well at about 1 ug/ml of mAb 10825 plus about 1 ug/ml of the free soluble peptide corresponding to the target epitope, about 1 ug/ml of mAb 10827 plus about 1 ug/ml of the free soluble peptide Met21-Ala30, about 1 ug/ml of mAb 10825 plus about 1 ug/ml of the control irrelevant peptide, and about 1 ug/ml of mAb 10827 plus about 1 ug/ml of the control irrelevant peptide were conducted.

Figure 7:
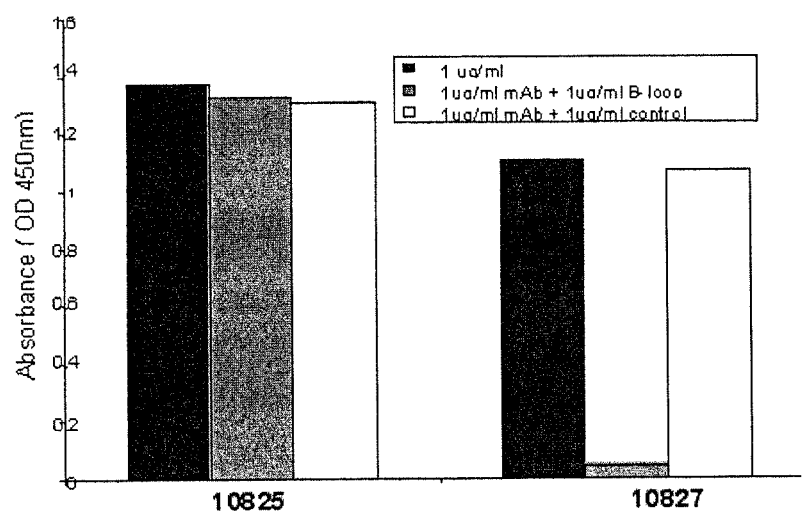
FIG. 7 illustrates a bar graph of mAb 10825 and mAb 10827 binding to rHuEGF in competition with a free soluble peptide derived from the neutralizing domain.

The optical density (OD) was measured at 450 nm. The results are illustrated in a bar graph with reference to FIG. 7. As illustrated in FIG. 7, of the two antibodies, mAb 10825 and mAb 10827, it is clear that the mAb 10827 antibody binds to the Met21-Ala30 neutralizing epitope and the mAb 10825 antibody does not. The mAb 10825 antibody is probably neutralizing by virtue of sterically hindering receptor binding by blocking a region of EGF conformationally proximal to the region defined by residues Met21-Ala30. Thus, the mAb 10827 antibody binds to the rEGF neutralizing epitope Met21-Ala30 in its native state, and was used in the following analysis of the synthetic EGF-CT-B vaccine precursors.

Example II: EGF Neutralizing Epitope Presentation

To determine whether or not the recombinant protein EGF-CT-B vaccine expressing the EGF on a termini of the CT-B sequence interferes with or otherwise influences any of the desired inherent characteristics of the EGF domain(s), specifically the correct conformational presentation of the EGF Met21-Ala30 epitope, and the ability of CT-B monomers to assemble into multimers (pentamer rings) under appropriate physico-chemical conditions, six recombinant proteins were created expressing the entire EGF coding region on the CT-B sequence at either the N (Test 1-Test 3) or C-terminus (Test 4-Test 6).

Test 1 and Test 4 include the recombinant protein EGF-CT-B vaccine expressing the full length EGF sequence directly on the CT-B domain. Test 2 and Test 5 include the synthetic EGF-CT-B vaccine expressing the full length EGF sequence separated from the CT-B domain by a short 3 amino acid peptide sequence. The recombinant protein EGF-CT-B vaccine expressing the EGF sequence on the N-terminal, includes SerGlyGly as the 3 amino acid peptide sequence, and includes a KpnI restriction site. The recombinant protein EGF-CT-B vaccine expressing the EGF sequence on the C-terminal, includes SerSerGly as the 3 amino acid peptide sequence, and includes a XhoI restriction site.

Test 3 and Test 6 include the recombinant protein EGF-CT-B expressing the full length EGF sequence separated from the CT-B domain by a short 5 amino acid peptide sequence. The recombinant protein EGF-CT-B expressing the EGF sequence on the N-terminal, includes GlyGlySerGlyGly as the 5 amino acid peptide sequence, and includes a KpnI restriction site. The synthetic EGF-CT-B expressing the EGF sequence on the C-terminal, includes SerSerGlyGlyGly as the 5 amino acid peptide sequence, and includes a XhoI restriction site. The short 3 and 5 amino acid peptide sequences serve both to distance the growth factor domain from the CT-B sequence, and also to allow a degree of freedom of movement of one domain relative to the other, thus reducing any potential steric hindrance.

Each of the six recombinant protein EGF-CT-B were cloned into a bacterial expression vector (pIMS147), such that the synthetic recombinant EGF-CT-B proteins could be expressed in *E. coli* periplasm, and purified by the inclusion of a C-terminal 6xHis tag. Each recombinant EGF-CT-B sequence was expressed, purified, and quantified by means of protein gel/Bradford assay.

The presentation of the EGF neutralizing epitope Met21-Ala30 in each of the six recombinant EGF-CT-B proteins was determined by ELISA. The recombinant EGF-CT-B proteins, including one terminal EGF domain were immobilized onto an ELISA plate. The EGF Met21-Ala30 epitopes were detected with the mAb 10827 antibody (Santa Cruz).

The ELISA plate was coated with serial 2-fold dilutions of synthetic EGF-CT-B 6-His purified proteins and incubated at about 37° C. for about 1 hour. The plate was washed and blocked with about 2% MPBS, as described above. Washing involved pipetting about 200 ul PBS or PBST into each well, inverting the plate and flicking to empty the wells, and repeating. The mAb 10827 antibody was then added to all the wells at about 1 µg/ml and incubated at about room temperature for about 1 hour. The plate was washed once more and an anti-mouse Horse-Raddish Peroxidase (HRP) was added to the wells and incubated for about a further 1 hour. The plate was washed again and developed using SureBlue TMB.

Upon adding the SureBlue TMB substrate, the HRP conjugated to the secondary antibody enzymatically processes the substrate to yield a blue product. The reaction was observed and monitored until it was decided that the color intensity has reached a sufficient level. (If color begins to appear in the control wells, which contain no primary antibody, then the reaction is stopped at this point). The reaction is stopped by addition of about 50 ul H2SO4 which destroys HRP activity. It also changes the color of the reaction product from blue to yellow. This can then be measured in a plate reader at about 450 nm absorbance.

Figure 8:
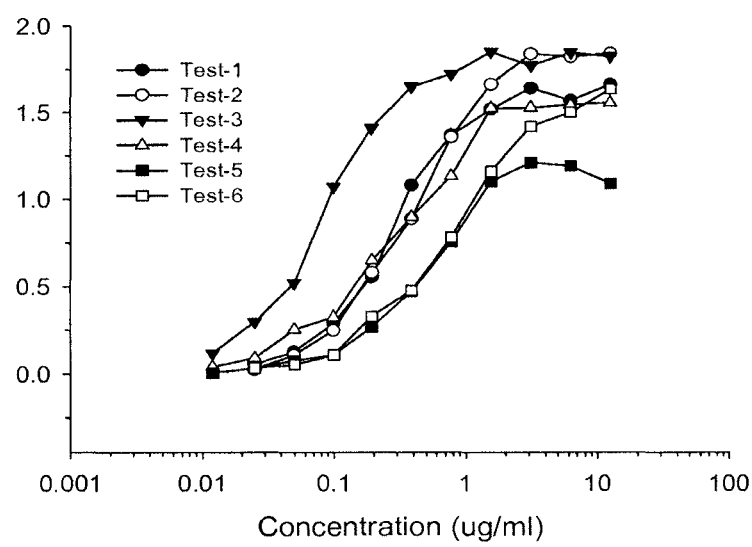
FIG. 8 illustrates a line graph of the binding of anti-EGF neutralizing domain mAb 10827 to 6 EGF-CT-B synthetic proteins adsorbed directly onto ELISA plates.

The results of the binding ELISAs are illustrated in a line graph with reference to FIG. 8. As illustrated in FIG. 8, the mAb 10827 antibody was able to bind to all six recombinant EGF-CT-B 6-His purified proteins, demonstrating that in each formulation the EGF-Met21-Ala30 epitope is presented in its native conformation and is accessible to components of the immune system.

Figure 9:
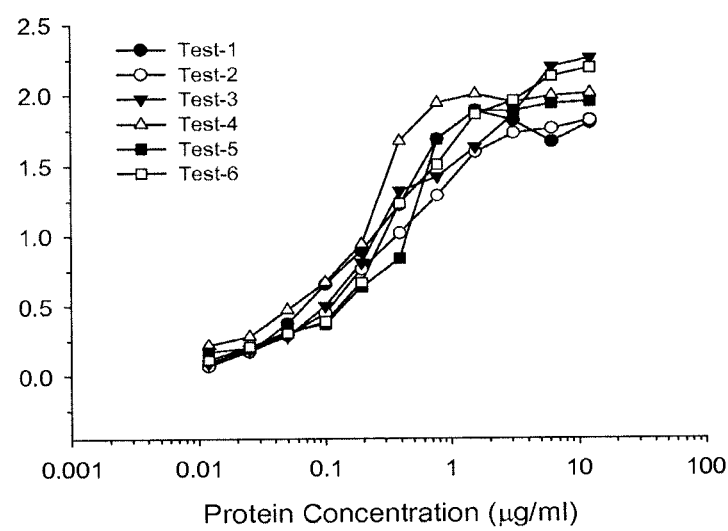

In order to confirm that the synthetic recombinant EGF-CT-B protein included expressions of the EGF domain and the CT-B sequence, a second ELISA was performed whereby rather than adsorbing the recombinant protein directly onto the plates, the recombinant protein was instead captured using a rabbit anti-CT-B antibody (Antibodies On-Line), as shown in FIG. 9. As this 'capture' antibody is specific to native CT-B, the assay demonstrates that the detected EGF neutralizing domains are components of a larger recombinant protein that includes a correctly folded CT-B domain.

Example III: EGF-CT-B Protein Multimer Assembly

Figure 10:
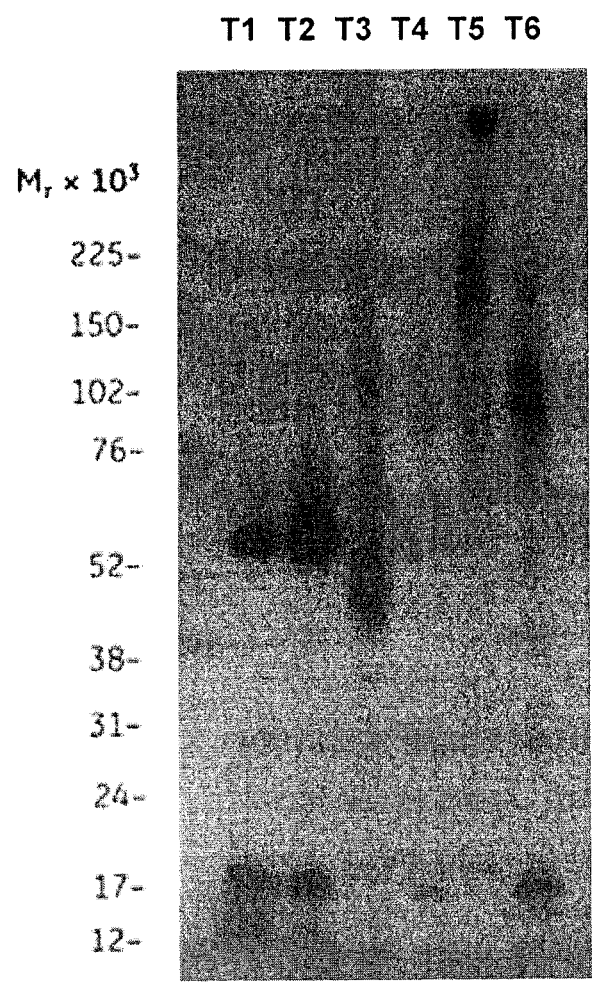

In order to examine the effect of expressing a structural domain comprising a growth factor on the termini of the CT-B derived recombinant protein on assembly of multimers from monomeric sub-units, synthetic proteins Test 1-Test 6 were run on an SDS-PAGE gel under native conditions (non-reduced, non-boiled). The synthetic recombinant EGF-CT-B proteins were then transferred onto a nitro-cellulose membrane by electro-blotting, and were probed using a rabbit anti-CT-B antibody (as described above in example II). Binding of a secondary HRP-labeled anti-rabbit antibody was detected via the light emitted using ECL substrate on autoradiograph film. As illustrated in FIG. 10, the Western blot confirms the presence of high molecular weight CT-B, indicating that the synthetic EGF-CT-B monomer proteins are able to assemble into multimers via the CT-B domain.

Figure 16:
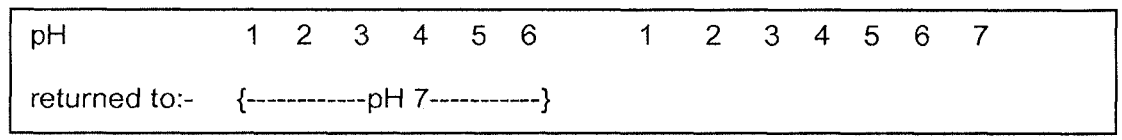

In a separate experiment, duplicate samples of native (non-boiled or reduced) CT-B protein were incubated for 5 min. at a range of different pH values from pH 1.0 to 7.0. Following incubation, one of each duplicate sample was neutralized back to pH 7.0 for one hour. All samples were then run on an SDS-PAGE gel, Western blotted, and protein detected with anti-CTB antibody (FIG. 16). This demonstrates that i) CTB pentamers can be reduced to monomers at pH 3.0 or below in 5 min., and ii) that returning to neutral pH restores the formation of pentamers. It has previously been demonstrated that a chimeric protein comprising a CT-B protein fused to a camelid antibody binding site and tags via a suitable linker (molecular weight of ~16 kDa) can be made to form functionally active pentamers (Li et. al., 2009 Molecular Immunology 46; 1718-1726).

Example IV: Bivalent Synthetic EGF-CT-B Proteins

In an illustrative embodiment, two additional synthetic recombinant EGF-CT-B proteins were created, in which i) a full length EGF gene is expressed at both the N- and C-termini, separated from the CT-B gene by the three amino acid sequence as described for Test-2 and Test-5 above, and designated 'E2', or ii) a truncated EGF including the Met21-Ala30 neutralizing epitope is expressed at both termini of the CT-B gene as above, and designated 'B2'. Both recombinant proteins were cloned into the *E. coli* expression vector pIMS147 as described above. Both recombinant EGF-CT-B proteins were expressed and purified as described previously, and assayed for the presence of correctly folded CT-B domain and presentation of EGF neutralizing epitope Met21-Ala30 in the correct conformation. The results are illustrated in a line graph with reference to FIG. 11. As illustrated in FIG. 11, both of the E2 and B2 recombinant EGF-CT-B proteins comprise both a CT-B domain and at least one functionally correct EGF Met21-Ala30 epitope displayed so as to be accessible to an antibody.

Figure 12:
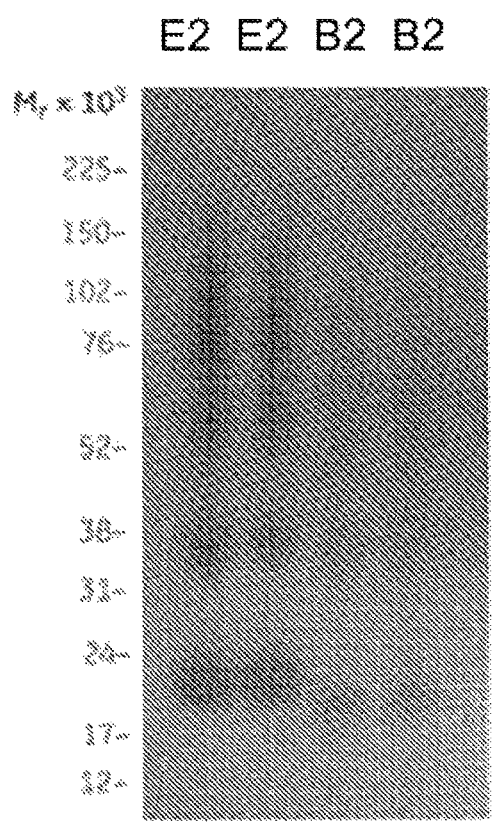

Further analysis involved running samples of purified E2 and B2 recombinant EGF-CT-B proteins on non-denaturing SDS-PAGE gels at pH 7.0 without first boiling the samples, and transferring to nitrocellulose membranes via electrotransfer. The transferred proteins were detected using the AbOL (Antibodies On-Line) anti-CT-B rabbit polyclonal antibody and an HRP-labeled anti-rabbit antibody. As illustrated in FIG. 12, the Western blot indicates that the CT-B domain-containing recombinant proteins exist both as monomers, and have also formed into a series of oligomeric multimers comprising dimers, trimers, tetramers and pentamers.

Example V: EGF-CT-B Protein Sequence

One example of a sequence of a synthetic recombinant EGF-CT-B protein is illustrated in FIG. 13. As illustrated in FIG. 13, the sample sequence illustrates the synthetic protein sequence including two full length EGF sequences, which are underlined, and a CT-B sequence, which is italicized.

Example VI: EGF-CT-B Protein Sequence

Another example of a sequence of a synthetic recombinant EGF-CT-B protein is illustrated in FIG. 14. As illustrated in FIG. 14, the sample sequence illustrates the protein sequence including two EGF neutralzing domain sequences, which are underlined, and a CT-B sequence, which is italicized.

Example VII: EGF-CT-B Protein Sequence

Figure 15:
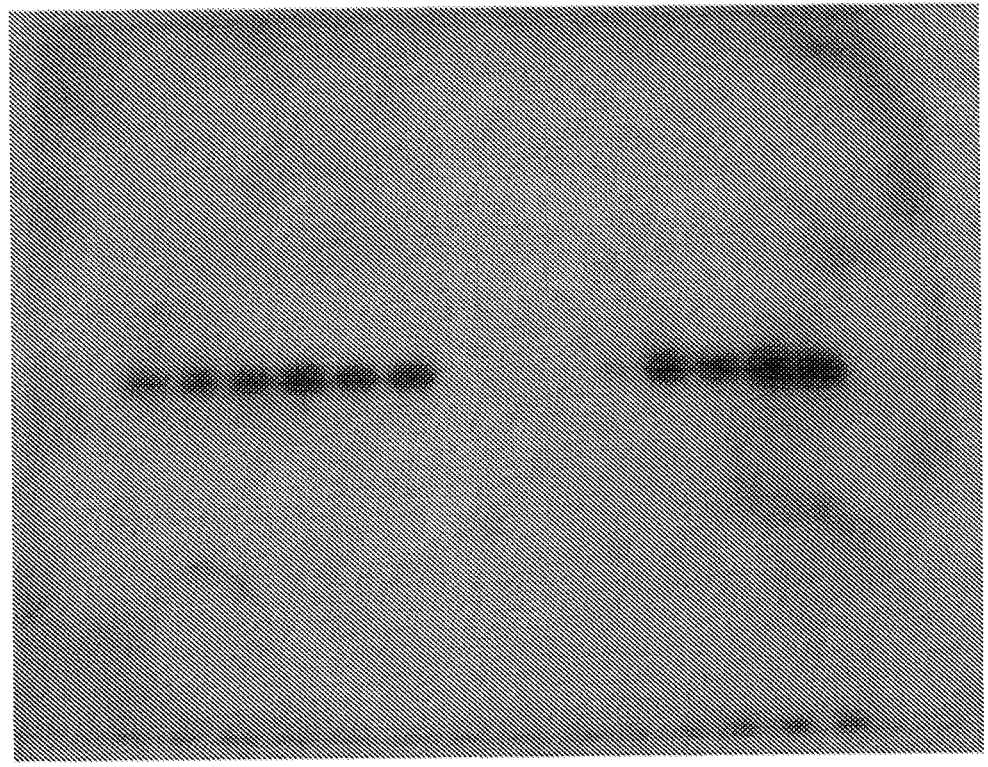

Yet another example of a sequence of a recombinant EGF-CT-B protein is illustrated in FIG. 15. As illustrated in FIG. 15, the sample sequence illustrates the protein sequence including partial sequences of the EGF molecule including the EGF neutralizing domain (Cys6 to Cys31), which are underlined, and a CT-B sequence, which is italicized.

Example VIII: EGF-CT-B Protein Sequences Including Linkers

In other illustrative embodiments, additional recombinant EGF-CT-B proteins including one or more linkers or spacers are disclosed herein. One or more of the embodiments described above include EGF fused to CT-B at one or both termini of the CT-B such that one gene ran directly into the next. These resulting recombinant or chimeric proteins essentially included EGF fused directly to CT-B. In other illustrative embodiments, the EGF and CT-B components of the chimeric protein are effectively separated by 3 or 5 amino acids, which form a flexible spacer or linker between the two domains. The following amino acids that can be used as linkers included but are not limited to the following: SSG, SSGGG, SGG, GGSGG, and GGGGS The addition of the linkers can reduce interferences, for example, from steric hindrance, and aid in the formation of pentamers by the CT-B domain. The linkers also enabled unique restriction sites to be introduced within the linkers to allow subsequent manipulation of the genetic constructs. In this example, eight constructs (T1-T6, E2, and B2) are described, having the sequences listed in the Table illustrated in FIG. 17. In one illustrative embodiment the restriction sites include but are not limited to the following: Xho1, Kpn1, BspE1, and Spe1.

Figure 18:
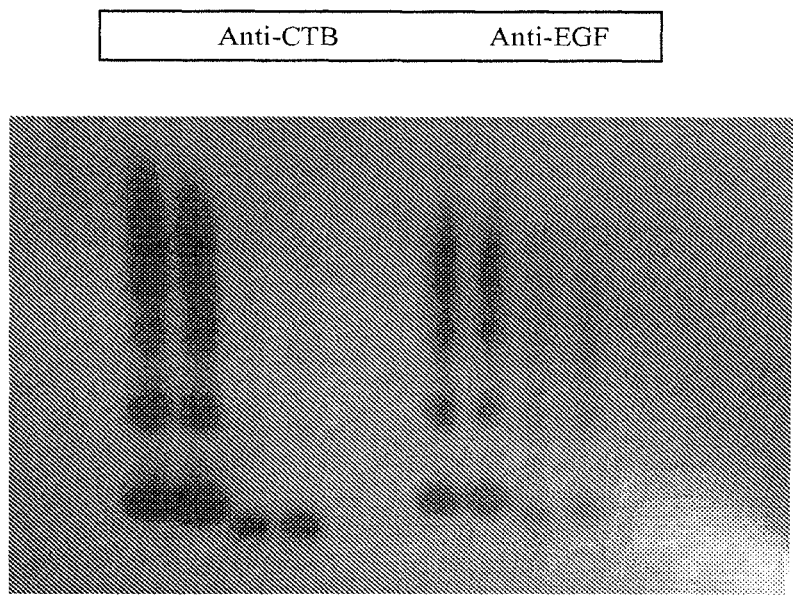

Western blot analysis of the constructs T1-T6, E2, and B2 was performed and are described below in connection with FIG. 18. As illustrated in FIG. 18, the Western blot of the constructs E2 and B2, there appears to be some interference, for example, steric hindrance and/or other interference, that caused the proteins produced to be comprised of a variety of oligomers, for example, monomer, dimer, trimer, etc. Alternatively, the concentration of protein present in samples may have influences oligomerization, as it is a dependent factor for native CTB pentamerization.

The lowest bands correspond to monomers, the next up to dimers etc. As B2 includes truncated EGFs, it appears to be smaller than E2, which is illustrated by B2 being lower on the Western blot.

A similar result is found for the constructs T1-T6, although the numbers and proportions of oligomers vary from construct to construct. Initially, it appeared that proteins with EGF on the N-terminus including the amino acid linkers might give a higher proportion of pentamer. However, subsequently it was found that the proportion of pentamer varied from batch to batch.

Figure 19:
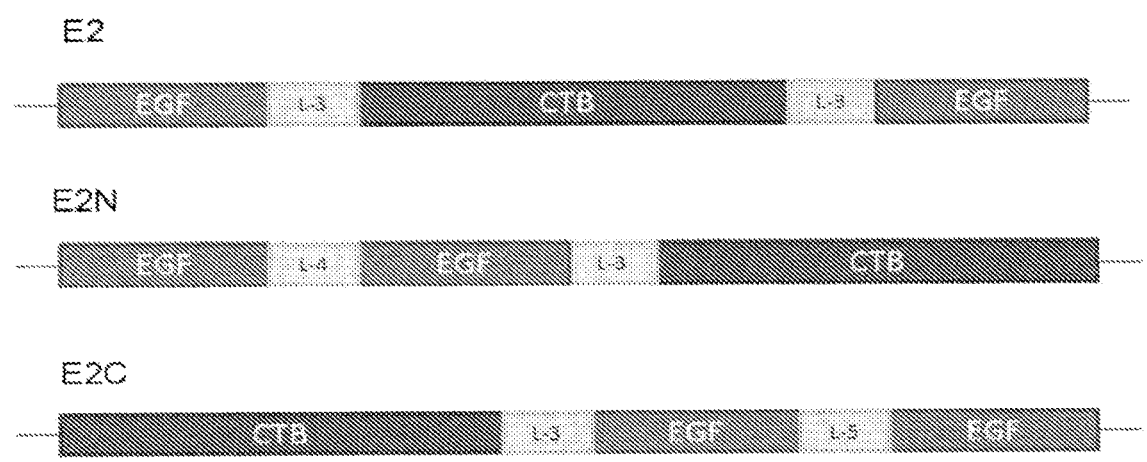
Figure 20:
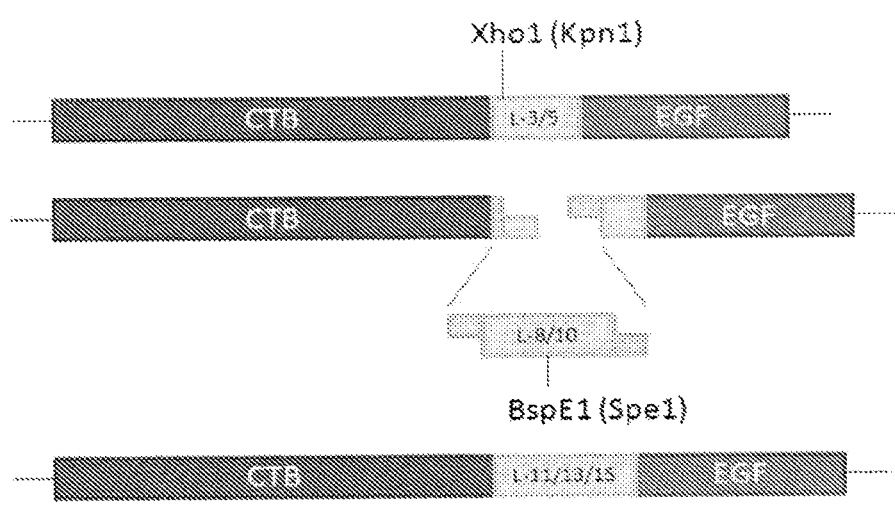

Since it was initially postulated that fusion at one or other terminus favors pentamerization, two tandem fusions in addition to the E2 construct were constructed and are illustrated in FIG. 19. The first tandem fusion, designated E2N, includes two consecutive EGF's at the N-terminus of the CT-B. Wherein L-3 is SGG, L-4 is GSSG The second fusion, designated E2C, includes two consecutive EGF's at the C-terminus of the CT-B Wherein L-3 is SSG, L-5 is GGSGG In an illustrative embodiment, the amino acid linker lengths at the N-terminus and the C-terminus were extended to determine whether or not the amino acid linker length at each end yields pentamer only, or perhaps that one end, the N-terminus or the C-terminus, yields a higher proportion of pentamer. Referring to FIG. 20, the N-terminus and C-terminus amino acid linkers were extended using the constructs T2/3 and T4/5, respectively. The illustration (FIG. 20) refers to the c-terminal fusion E2C. In this illustrative example, L3 is SSG, L5 is SSGGG, L8 is SSGGGSGG and L10 is SSGGGGSGGG. In the N-terminal version, the inserted linker spacers were about? and 9 residues in length. In that example the 4 linkers would be: L3 SGG, L5 GGSGG, L7 TSGGGSG and L9 TSGGGGSGG. Each of the linker-spacers can be inserted into each of the shorter L3 and L5 linkers. As a result, inserting L7 into L5 or L9 into L3 both yield linkers of 12 residues, HOWEVER they would have different sequences, termed 'a' and 'b' below. The N-terminus linkers were also extended to 10, 12 and 14 amino acids, and the C-terminus were extended to 11, 13 and 15 amino acids, as illustrated in FIG. 20. In this illustrative example L10 is SSGGGSGGSSG, L12a is GGSGGTSGGGSG, L12b is SGGTSGGGGSGG, and L14 is GGSGGTSGGGGSGG. Similarly, L11 is SSGGGSGGSSG, L13a SSGGGGGSGGGSSG, L13b SSGGGSGGSSGGG, and L15 SSGGGGGSGGGSSGGG.

Figure 21:
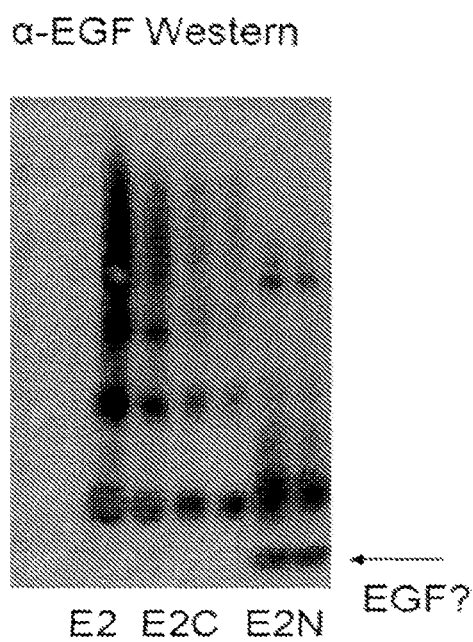

Referring to FIG. 21, Western blot analysis of the tandem EGF fusions, E2N and E2C, compared to the original bivalent construct with the original E2 demonstrate that both E2 and E2C produce many oligomers. E2N also produces oligomers, however there is a strong indication that the first EGF domain is being either expressed as a truncated protein, or is being cleaved off at some stage during expression/purification.

Figure 22:
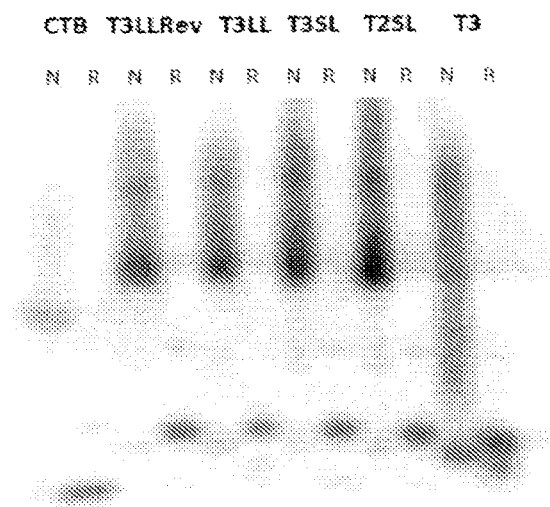

A comparative Western blot analysis was also performed on the monovalent 'T' constructs with the extended linkers, and is illustrated in FIG. 22. When the above linker extensions were introduced to the constructs already named T2 and T3 (N-terminal, 3 and 5 aa linkers respectively), we get T2SL (Short extended Linker, i.e. L10), T2LL (Long Linker, L12a) T3SL (Short linker L12b), and T3LL (Long Linker L14). Similarly the N-terminal T5 and T6 constructs become TSSL (with L11), TSLL (with L13a), T6SL (with L13b) and T6LL (with L15).

When the linker spacers are inserted, they can actually be cloned in either of two directions, giving quite different sequences. Wherever possible, sufficient clones were sequenced to find one with the insertion in the desired direction. In the case of T3LL-Rev, initially we only had a clone with the desired linker length (i.e. 14 aa's) but with the insert in the 'wrong' orientation. It does serve to illustrate how the precise sequences of these linkers isn't necessarily critical, at least as far as acting as a physical spacer. The actual linker sequence of T3LL-Rev would be GGSGGTRPSTAATS. (underlined=inverted section).

As illustrated in the Western blot illustrated in FIG. 22, N and R refer to native and reduced/denatured protein, respectively. The first two lanes illustrate wild type CT-B as a pentamer (native) and a monomer (reduced). As illustrated in the other lanes, it can be seen that T3 (including the 5 amino acid linker) produced some oligomers of various sizes, however all N-terminus constructs with longer linkers produce primarily pentamer when run under native conditions.

Figure 23:
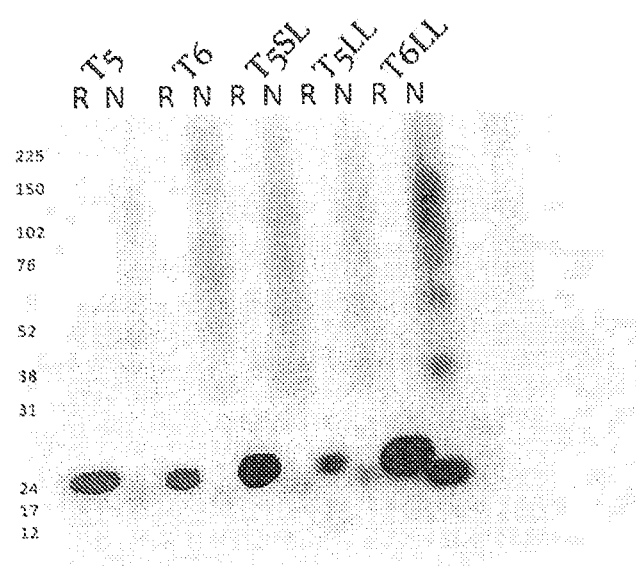
Figure 25:
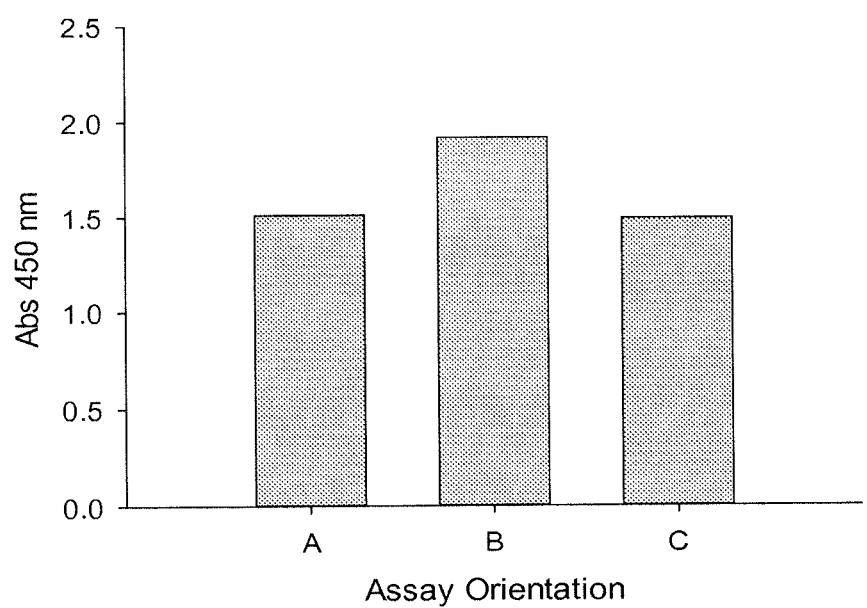

In contrast, as illustrated in FIG. 23, the Western blot of the C-terminus constructs produced multiple bands under native conditions even with extended linkers.

Based on this data, the tandem N-terminus fusion of EGF to CT-B appears to be of significant interest. Additionally, the first linker (between the two EGF domains) may be extended to attempt to prevent the truncation/proteolysis described above with the E2N construct, and to allow flexibility when introducing alternative growth factors. The Sequence for the N-terminus FUSION of EGF to CT-B with the extended first linker) is as follows:

```
H H H H H H I E G R N S D S E C P L S H D G Y C L
H D G V C M Y I E A L D K Y A C N C V V G Y I G E
R C Q Y R D L K W W E L R G G S G G T S G G G G S
G G T P Q N I T D L C A E Y H N T Q I H T L N D K
I F S Y T E S L A G K R E M A I I T F K N G A T F
```

-continued

```
Q V E V P G S Q H I D S Q K K A I E R M K D T L R
I A Y L T E A K V E K L C V W N N K T P H A I A A
I S M A N
```

While the homogeneous recombinant proteins expressing or incorporating EGF B-loop epitopes have been described and illustrated in connection with certain embodiments, many variations and modifications will be evident to those skilled in the art and may be made without departing from the spirit and scope of the disclosure.

Example IX: Bi-Specific IGF1-EGF-CTB Protein (a)

In order to establish the feasibility of targeting more than one growth factor with a single synthetic recombinant protein, a gene encoding the human insulin-like growth factor 1 (IGF1) was synthesized including short flanking regions to enable cloning into the construct E2N described in example VIII. Briefly, the N-terminal EGF gene was excised from the vector by digesting the DNA with the restriction endonucleases Nco1 and Xho1. It was then replaced with the similarly digested human IGF1 gene using methods familiar to those skilled in the art. The resulting DNA vector was sequenced to confirm that it encoded the required recombinant gene in such a way as to allow the recombinant protein to be expressed as designed. The sequence of the novel recombinant protein is illustrated in FIG. 24.

Subsequently, the protein generated by the expression of the aforementioned vector was analyzed by ELISA to demonstrate that both growth factors can be simultaneously displayed to components (i.e. antibodies) of the mammalian immune system. Briefly, wells of an ELISA plate were coated with an appropriate dilution of anti-CTB antibody and then blocked with PBS containing 2% milk powder as described previously. Samples of the recombinant protein were applied to the plate and incubated for 1 hour at room temperature. After washing, different wells prepared as described were then incubated with 1/1000 (or as per supplier's recommendations) of either i) mouse anti-EGF antibody AbOL 10827 or ii) rabbit anti-human IGF1 2o antibody. After washing, the wells were incubated with an appropriate dilution of i) HRP-labeled anti-mouse antibody or ii) HRP-labeled anti-rabbit antibody and then developed as described previously. As illustrated in FIG. 25, the signals generated confirmed that both IGF and EGF are displayed in their native configurations. The signal generated by the anti-IGF antibody also confirms that IGF, EGF and CTB sequences are present in the same molecule due to the relative positions of the encoding DNA sequences in the expression vector.

Example X: Bi-Specific IGF1-EGF-CTB Protein (b)

In order to demonstrate that bi-specific recombinant proteins can be generated using the natural characteristic of CTB to form oligomers, the IGF gene described in example IX was modified by PCR using techniques familiar to those skilled in the art to enable it to be cloned into the T5 construct, replacing the EGF gene. The resulting recombinant protein included IGF sequences C-terminal to CTB sequences, and separated by a 3 amino acid linker (FIG. 26).

Samples of the above recombinant protein were combined separately with equal (molar) amounts of i) T2 protein and ii) T5 protein. Each of the mixtures was adjusted to pH 3.0 by the addition of buffered 10 mM Tris-HCL as required and incubated at 4° C. for 15 min to dissociate any oligomers present. The protein mixtures were then neutralized, and incubation continued for 60 min in order to encourage oligomerization. To detect the presence of hetero-oligomers, wells of an ELISA plate were coated with either mouse anti-EGF antibody or rabbit anti-IGF antibody, and blocked. After washing, IGF-CTB/T2 mix and IGF-CTB/T5 mix were applied separately to either wells coated with anti-EGF antibody or with anti-IGF antibody, and incubated for 60 min at room temperature.

After washing, antibody specific to the growth factor not targeted by the coating antibody was added and incubated for 60 min. Thus, rabbit anti-IGF antibody was applied to wells coated with mouse anti-EGF antibody, and vice-versa. After washing to remove unbound 2o antibody, HRP-labeled anti-mouse or HRP-labeled anti-rabbit antibody was applied as appropriate to target the 2o antibody. The results are illustrated in FIG. 27, and demonstrate that anti-EGF coating antibody can capture and immobilize protein containing IGF sequences. Similarly, anti-IGF antibody can capture and immobilize protein that includes EGF sequences. In both cases, this is caused by oligomerization of IGF and EGF-containing monomers such that both are present. Moreover, the hetero-oligomers are able to form when both growth factors are located at opposite termini of the CTB component (i.e. IGF-CTB and T2) and when both growth factors are on the same (C) terminus (i.e. IGF-CTB and T5). The assay also works in either orientation.

Example XI: Diverse Growth Factor Presentation

In order to further demonstrate the flexibility of the present invention, a panel of recombinant proteins were generated that included sequence derived from CTB together with additional sequence derived from one or more of a range of growth factors and representing a range of domains of varying size according to FIG. 28 using standard techniques familiar to those practiced in the art. Samples of each of the proteins was prepared by expression of the genetic construct in *E. coli* and purified using IMAC via the hexa-histidine tag N-terminal to each protein. Purified recombinant proteins were assayed by ELISA to demonstrate that the each of the different sequences was present and displayed correctly using antibodies specific for each sequence (FIG. 29). A native protein was run with samples of the recombinant protein including sequences derived from mTGF B1 and CTB and a Western blot prepared (FIG. 30). Protein was detected with α-CTB antibody and showed that under the conditions used the recombinant chimeric protein was able to form stable pentamers, retaining this characteristic of CTB.

Example XII: Growth Factor Receptor Presentation

In order to demonstrate that the technology described in the present disclosure is applicable to the functional display of proteins other than growth factors, recombinant proteins including sequences derived from growth factor receptors and CTB were generated, and shown to present such sequences in a natural conformation in conjunction with CTB sequences. DNA encoding the protein sequence of human TGF-beta1 was cloned upstream of the CTB gene. by replacing the EGF coding DNA from the T3LL clone using standard techniques familiar to those practiced in the art. This construct was used to generate a recombinant protein including both human TGF-beta1 and CTB sequences (FIG. 31*a*). Likewise, a second recombinant protein was generated that included sequences of the extra-cellular ligand-binding domain of the human TGF Beta receptor 2 and CTB (FIG. 31*b*).

The simultaneous presentation of both TGF-Beta R2 and CTB sequences on a single recombinant protein was established by capture ELISA. Briefly, wells of an ELISA plate were coated with i) mouse anti-CTB antibody or ii) goat anti-TGF Beta R2 antibody and blocked with PBS containing milk powder. Samples of the recombinant protein according to FIG. 31*b* were then contacted to the wells and incubated for about 1 hour. Following washing, the wells were contacted with i) goat anti-TGF Beta R2 antibody or ii) mouse anti-CTB antibody respectively and incubated for 1 hour. Following washing, the wells were contacted with i) HRP-labeled anti-sheep (goat) antibody and ii) HRP-labeled anti-mouse antibody respectively and incubated for about 1 hour. The plate was developed with TMB substrate and color intensity measured at 450 nm. The assay demonstrated that both TGF-beta R2 and CTB sequences were present on the same chimeric recombinant protein (FIG. 32).

In order to demonstrate that both TGF-Beta1 and TGF Beta R2 were both presented separately with CTB sequences in a native configuration, the interaction between TGF beta1 and its natural receptor was determined by ELISA. Briefly, wells of an ELISA plate were coated with mouse anti-CTB antibody as blocked. The wells were then contacted with the recombinant protein containing human TGF-beta1 and CTB sequences as described in FIG. 31*a* and incubated for about 1 hour. After washing, the wells were contacted with the recombinant protein containing human TGF-betaR2 and CTB sequences as described in FIG. 31*b* and incubated for about 1 hour. The wells were washed and then contacted with goat anti-TGF Beta R2 antibody for 1 hour. Finally, the wells were washed and contacted with HRP-labeled anti-sheep (goat) antibody for about 1 hour. The plate was developed with TMB substrate and read at 450 nm. FIG. 33 illustrates that the two recombinant proteins are able to reproduce the natural receptor-ligand binding interaction, and that this is not disturbed by the anti-receptor antibody used in the assay.

Example XIII: Immune Responses of Mice to Recombinant Protein Formulations

In another experiment groups of mice were immunized with recombinant proteins including sequences from CTB and one or more growth factors according to the present disclosure in order to assess the effects of various formulations on immune responses of said mice. Six groups of mice, each comprising six mice were immunized, with a different recombinant protein formulation according to the schedule described below.

Unless otherwise stated, mice were immunized with 25 μg recombinant protein in 75 μl buffer, emulsified in 75 μl montanide adjuvant. Immunogens were administered via i.m. injection at day 0 and day 14. Serum samples were taken at day 0 (pre-immunization) and day 28 and were analyzed for the presence of IgG antibodies against the growth factor sequences contained within the immunizing recombinant protein. The groups of mice were immunized with the following antigens:

Group 1: SB1, 75 µl (25 µg) recombinant protein including human IGF and CTB sequences according to FIG. 26 emulsified with 75 µl montanide;

Group 2: SB2, 75 µl (25 µg) recombinant protein including human EGF and CTB sequences as described in example VIII and referred to as T3LL, emulsified with 75 µl montanide;

Group 3: SB3, 75 µl (25 µg) recombinant protein including human IGF, human EGF and CTB sequences according to FIG. 24 and as described in example IX, emulsified with 75 µl montanide;

Group 4: SB4, 37.5 µl (12.5 µg) SB1 and 37.5 µl (12.5 µg) SB2 combined by the method as described in example X and including oligomers containing both IGF-CTB and EGF-CTB, emulsified with 75 µl montanide;

Group 5: SB3, 75 µl (25 µg) SB1, as for Group 1, except emulsified with 20 µl Matrix-M adjuvant; and Group 6: SB6, 37.5 µl (12.5 µg) SB1 emulsified with 37.5 µl montanide, followed after 5 min by 37.5 µl (12.5 µg) SB2 emulsified with 37.5 µl montanide and administered via a different location.

Immediately prior to, and 14 days after immunization, blood samples were taken and serum analyzed by ELISA for the presence and relative titres of IgG antibodies against the growth factor component of the recombinant protein immunizing antigens. ELISA plates were coated with commercially available recombinant human IGF or EGF at 1 µg/ml concentration. After blocking and washing, serum from subject mice at various dilutions was applied to wells and incubated for 1 hour at room temperature. Un-bound antibody and other proteins were removed by washing, and bound mouse IgG detected with HRP-labeled anti-mouse antibody.

All six groups included animals that raised a specific immune response to the growth factor component of the immunogenic recombinant chimeric proteins. It is evident that stronger responses are seen to EGF than to IGF throughout, including groups where sequences from only one growth factor was included (Groups 1 and 2, FIGS. 34 and 35). Without being bound to any particular theory, this is probably a reflection of the degrees of homology between the mouse and human proteins, whereby the EGF's differ by 15/53 residues and the IGF's only differ at 4 of 70 residues. It is also notable that differences between the responses of individual animals within a group are often greater than differences between groups to the same antigen.

The use of Matrix-M rather than Montanide as adjuvant (Group 5 compared to Group 1, FIGS. 40 and 34) resulted in a poorer response, with one of the mice not responding at all, and four other samples needing to be screened at much higher concentrations than with Montanide.

Groups 3, 4 and 6 received proteins that included sequences from both EGF and IGF, the difference being the formulation or administration. Group 3 mice, receiving recombinant protein that included both EGF and IGF sequences on each protein molecule, all responded to EGF though two of the six did not show an α-IGF response (FIGS. 36 and 37). Groups 4 and 6 mice also all generated antibodies to EGF (FIGS. 38, 39 and 41). In Group 4 one animal did not respond to IGF and another gave only a very weak response. Only in Group 6, where EGF and IGF-containing proteins were administered separately and at different locations, did all 6 animals mount a response to IGF.

Example XIV: Generic Single-Step Purification

A simple first-stage purification process is desired that can be applied to any and all of the immunogenic recombinant proteins detailed in the present disclosure. Ideally, the purification will not require the inclusion of an affinity tag such as hexa-histidine, MBP, FLAG etc. The recombinant proteins of the present disclosure are related in that they all include at least some sequence derived from the *Vibrio cholera* CT-B toxin sub-unit, or a synthetic functional equivalent. It is envisaged that purification could be achieved by the use of monoclonal or polyclonal antibodies, however monoclonal antibodies are expensive to produce. Polyclonal antibodies are less expensive, however it is likely that variations in performance will be seen between batches from the same animal, and between individual animals. Immuno-affinity purification also requires harsh conditions such as low pH to elute target protein that can adversely affect the target protein, and will limit the re-use of the affinity matrix. It also involves the introduction of additional protein into the production process, which is preferably avoided.

In the native CT holotoxin, the toxin binds to monoganglioside Gm1 (FIG. 42) found on the surface of most mammalian cells, including epithelial cells of the respiratory tract and gut. Binding is effected by the CT-B sub-unit, and only CT-B oligomers bind to Gm1. It is therefore envisaged that CTB immobilized onto a suitable support could be used for the purification of the immunogenic recombinant proteins of the present disclosure. The use of CTB is not thought to be a preferred method however for several reasons, notably that CTB is only available commercially as material purified from bovine brain. The use of animal material, and the use of bovine brain tissue in particular is not suitable for use in production of therapeutic products.

The binding of CTB to Gm1 is known to involve a terminal galactose moiety on the branched glyco-molecule Gm1 binding to two adjacent CTB sub-units. It is therefore envisaged that galactose immobilized to a suitable solid support would provide a generic means to purifying the recombinant proteins of the present disclosure. To assess the applicability of this approach, the gene encoding CTB was cloned into a bacterial protein expression vector designed for periplasmic protein recovery using techniques familiar to those practiced in the art, and transformed into various strains of *E. coli* bacteria. Galactose-sepharose resin (FIG. 43) was sourced from Pierce (Pierce Cat No. 20372). Fifty milliliter cultures of the CTB-expressing clones in XL1-Blue, BL21 and TG1 *E. coli* strains were grown and induced to express recombinant CTB overnight at 37° C. The cells were harvested by centrifugation and the clarified media retained for extraction of CTB. The periplasmic contents of the cell pellets were released by osmotic shock using standard methods familiar to those practiced in the art yielding 10 ml per culture.

The galactose sepharose resin was washed with 200 mM NaCl, 50 mM Tris HCl, 5 mM EDTA pH 7.5 (TEN buffer) according to manufacturer's instructions. NaCl, Tris-HCl pH 7.5 and EDTA were added to the conditioned media and periplasmic fractions to a final concentration of 200 mM NaCl, 50 mM Tris-HCl and 5 mM EDTA. 0.5 ml washed galactose sepharose was added to each conditioned media and periplasmic fraction, and incubated with agitation at 4° C. for 2-3 h. The resin was recovered into BioRad columns and washed with 30 bed volumes of ice-cold TEN buffer. The bound protein was eluted by re-suspending the resin in 0.5 ml 1 M galactose in PBS and incubating for 10 min. The column was drained and the eluate retained for analysis. The elution step was repeated several times, and fractions analyzed for the presence of CTB. Almost all of the expressed CTB protein was found in the culture media. Samples of pre-purification conditioned media and periplasmic fraction, together with pooled column eluates containing purified CTB (from the media) were analysed by SDS-PAGE and compared with His-tagged CTB purified by IMAC (FIG. 44). It can be seen that highly purified CTB was obtained from the culture supernatants of all three strains, with XL1-Blue cells giving the highest yields (Lanes 4, 7 and 10). The purity compares well with that seen from IMAC purification (Lane 11), and includes significant pentameric protein.

ADDITIONAL EMBODIMENTS

In another illustrative embodiment, a vaccine comprised of a homogeneous recombinant protein for improving the presentation of and increasing the number of tumor antigen epitopes as elements of a synthetic immunogenic recombinant protein is disclosed herein. In one illustrative embodiment, a vaccine formed from a recombinant protein expressing all or portions of a polypeptide sequence and a tumor antigen is described herein.

In an illustrative embodiment, the recombinant proteins disclosed herein may include or express a high proportion of a protein sequence derived from tumor antigens and/or epitopes thereof, as a function of total molecular weight. These tumor antigen epitopes can be multiple copies of whole or part of a single tumor antigen, or copies of whole or part of more than one different tumor antigen.

In an illustrative embodiment, the recombinant protein is an immunogenic protein molecule expressing one or more sequences that fold into a physical structure, for example expressing one or more sequences of a cholera toxin B (CT-B) protein from *Vibrio cholera* or a synthetic equivalent, and expressing one or more sequences of one or more tumor antigens or parts thereof.

In an illustrative embodiment, the sequence of the tumor antigen may include a sequence of a Prostate Specific Antigen (PSA) or part thereof. In other illustrative embodiments, the tumor antigen may include a full length or part thereof of one or more of the following tumor antigens, including, but not limited to, PSA, and other tumor antigens.

In another illustrative embodiment, a protein comprised of a homogeneous recombinant protein for improving the presentation of and increasing the number of receptor binding sites as elements of a immunogenic recombinant protein is disclosed herein. In one illustrative embodiment, a recombinant protein expressing all or portions of a polypeptide sequence and a receptor is described herein.

In an illustrative embodiment, the recombinant proteins disclosed herein may include or express a high proportion of a protein sequence derived from receptors and/or binding sites thereof, as a function of total molecular weight. These binding sites can be multiple copies of whole or part of a single receptor, or copies of whole or part of more than one different receptor.

In an illustrative embodiment, the recombinant protein is an immunogenic protein molecule expressing one or more sequences that fold into a physical structure, for example expressing one or more sequences of a cholera toxin B (CT-B) protein from *Vibrio cholera* or a synthetic equivalent, and expressing one or more sequences of one or more receptors or parts thereof.

In an illustrative embodiment, the sequence of the receptor may include a sequence of a Human Epidermal growth factor Receptor 2 (Her2) or part thereof and/or a Human Epidermal growth factor Receptor 3 (Her3) or part thereof. In other illustrative embodiments, the receptor may include a full length or part thereof of one or more of the following receptors, including, but not limited to, Her2, Her3, and other receptors.

In other illustrative embodiments, the recombinant protein is an immunogenic protein molecule expressing one or more sequences that fold into a physical structure, for example expressing one or more sequences of a CT-B or a synthetic modified variant, and expressing various combinations of one or more sequences of one or more growth factors or parts thereof, one or more sequences of one or more tumor antigens or parts thereof, and one or more sequences of one or more receptors or parts thereof.

In an illustrative embodiment, the recombinant protein includes expressions or sequences of one or more growth factors or parts thereof and one or more sequences of one or more tumor antigens or parts thereof. In one embodiment, the recombinant protein includes one or more sequences of a CT-B or a synthetic modified variant, a PSA or part thereof, and an IGF-1 or part thereof.

In another illustrative embodiment, the recombinant protein includes expressions or sequences of one or more growth factors or parts thereof and one or more sequences of one or more receptors or parts thereof. In one embodiment, the recombinant protein includes one or more sequences of a CT-B or a synthetic modified variant, a Her2 or part thereof, and an IGF-1 or part thereof. In another embodiment, the recombinant protein includes one or more sequences of a CT-B or a synthetic modified variant, a Her2 or part thereof, a Her2 or part thereof, and a PDGF or part thereof.

In another illustrative embodiment, the recombinant protein includes expressions or sequences of one or more tumor antigens or parts thereof and one or more sequences of one or more receptors or parts thereof.

In yet another illustrative embodiment, the recombinant protein includes expressions or sequences of one or more growth factors or parts thereof, one or more sequences of one or more tumor antigens or parts thereof, and one or more sequences of one or more receptors or parts thereof.

In any of the embodiments described above, in addition to expressing one or more copies of a single tumor antigen, receptor, and/or growth factor, presented as a single tumor antigen, receptor, and/or growth factor or part thereof per physical site, and/or as chains of repetitive tumor antigen, receptor, and/or growth factor sequences (for example, n=1 to 10). The recombinant proteins according to the disclosure may also include expressions of one or more neutralizing domains or binding sites from two or more different tumor antigens, receptors, and/or growth factors present as single or as chains at different positions within the sequences of the recombinant proteins. For example, the recombinant proteins may include expressions or sequences of a full length or a portion of two to four different tumor antigens, receptors, and/or growth factors, and/or a full length or a portion of one or more tumor antigens, receptors, and/or growth factors as single epitopes or binding sites or as two or more tandem repeats.

The resulting proteins are single polypeptides expressing a tumor antigen, receptor, and/or growth factor or one or more epitopes or binding sites thereof within the sequence of the recombinant proteins. In an illustrative embodiment, the sequences of the recombinant proteins expresses one or more portions of a CT-B sequence and presents the tumor antigen, receptor, and/or growth factor expression(s) including at least one or more expression(s) of epitopes or binding sites thereof on a surface of the immunogenic recombinant proteins in a natural conformation.

According to the disclosure, the expressions of the tumor antigen epitopes, receptor binding sites, and/or growth factor epitopes should be folded allowing their natural conformation to be substantially retained and presented to components of the host immune system in such a way as to elicit a robust host immune response. Examples of suitable natural protein models include, but are not limited to, cholera toxin B sub-unit, *listeria*, tetanus toxoid, diphtheria toxoid, bacteriophage coat protein, adenovirus and other viral coat proteins. Alternatively, non-natural 'synthetic' polypeptides may be used that fulfill the requirements of conferring immunogenicity to the whole protein and allowing appropriate presentation of tumor antigen epitopes, receptor binding sites, and/or growth factor epitopes to the host immune system.

Adjuvant

Certain illustrative embodiments as provided herein include recombinant proteins according to the disclosure within vaccine compositions and immunological adjuvant compositions, including pharmaceutical compositions, that contain, in addition to recombinant proteins at least one adjuvant, which refers to a component of such compositions that has adjuvant activity. An adjuvant having such adjuvant activity includes a composition that, when administered to a subject such as a human (e.g., a human patient), a non-human primate, a mammal or another higher eukaryotic organism having a recognized immune system, is capable of altering (i.e., increasing or decreasing in a statistically significant manner, and in certain preferred embodiments, enhancing or increasing) the potency and/or longevity of an immune response. In certain illustrative embodiments disclosed herein a desired antigen and or antigens contain within a protein carrier, and optionally one or more adjuvants, may so alter, e.g., elicit or enhance, an immune response that is directed against the desired antigen and or antigens which may be administered at the same time or may be separated in time and/or space (e.g., at a different anatomic site) in its administration, but certain illustrative embodiments are not intended to be so limited and thus also contemplate administration of recombinant protein in a composition that does not include a specified antigen but which may also include but is not limited to one or more co-adjuvant, an imidazoquinline immune response modifier.

Accordingly and as noted above, adjuvants include compositions that have adjuvant effects, such as saponins and saponin mimetics, including QS21 and QS21 mimetics (see, e.g., U.S. Pat. No. 5,057,540; EP 0 362 279 B1; WO 95/17210), alum, plant alkaloids such as tomatine, detergents such as (but not limited to) saponin, polysorbate 80, Span 85 and stearyl tyrosine, one or more cytokines (e.g., GM-CSF, IL-2, IL-7, IL-12, TNF-alpha, IFN-gamma), an imidazoquinoline immune response modifier, and a double stem loop immune modifier (dSLIM, e.g., Weeratna et al., 2005 Vaccine 23:5263).

Detergents including saponins are taught in, e.g., U.S. Pat. No. 6,544,518; Lacaille-Dubois, M and Wagner H. (1996 Phytomedicine 2:363-386), U.S. Pat. No. 5,057,540, Kensil, Crit. Rev Ther Drug Carrier Syst, 1996, 12 (1-2):1-55, and EP 0 362 279 B1. Particulate structures, termed Immune Stimulating Complexes (ISCOMS), comprising fractions of Quil A (saponin) are haemolytic and have been used in the manufacture of vaccines (Morein, B., EP 0 109 942 B1). These structures have been reported to have adjuvant activity (EP 0 109 942 B1; WO 96/11711). The haemolytic saponins QS21 and QS17 (HPLC purified fractions of Quil A) have been described as potent systemic adjuvants, and the method of their production is disclosed in U.S. Pat. No. 5,057,540 and EP 0 362 279 B1. Also described in these references is the use of QS7 (a non-haemolytic fraction of Quil-A) which acts as a potent adjuvant for systemic vaccines. Use of QS21 is further described in Kensil et al. (1991. J. Immunology 146:431-437). Combinations of QS21 and polysorbate or cyclodextrin are also known (WO 99/10008). Particulate adjuvant systems comprising fractions of QuilA, such as QS21 and QS7 are described in WO 96/33739 and WO 96/11711. Other saponins which have been used in systemic vaccination studies include those derived from other plant species such as *Gypsophila* and *Saponaria* (Bomford et al., Vaccine, 10(9):572-577, 1992).

Escin is another detergent related to the saponins for use in the adjuvant compositions of the embodiments herein disclosed. Escin is described in the Merck index (12.sup.th Ed.: entry 3737) as a mixture of saponin occurring in the seed of the horse chestnut tree, *Aesculus hippocastanum*. Its isolation is described by chromatography and purification (Fiedler, Arzneimittel-Forsch. 4, 213 (1953)), and by ion-exchange resins (Erbring et al., U.S. Pat. No. 3,238,190). Fractions of escin (also known as aescin) have been purified and shown to be biologically active (Yoshikawa M, et al. (Chem Pharm Bull (Tokyo) 1996 August; 44(8): 1454-1464)). Digitonin is another detergent, also being described in the Merck index (12th Ed., entry 3204) as a saponin, being derived from the seeds of *Digitalis purpurea* and purified according to the procedure described by Gisvold et al., J. Am. Pharm. Assoc., 1934, 23, 664; and Rubenstroth-Bauer, Physiol. Chem., 1955, 301, 621.

Other adjuvants or co-adjuvants for use according to certain herein disclosed embodiments include a block co-polymer or biodegradable polymer, which refers to a class of polymeric compounds with which those in the relevant art will be familiar. Examples of a block co-polymer or biodegradable polymer that may be included in a vaccine composition or a immunological adjuvant include Pluronic® L121 (BASF Corp., Mount Olive, N.J.; see, e.g., Yeh et al., 1996 Pharm. Res. 13:1693), Certain further illustrative embodiments contemplate immunological adjuvants that include but are not limited to an oil, which in some such embodiments may contribute co-adjuvant activity and in other such embodiments may additionally or alternatively provide a pharmaceutically acceptable carrier or excipient. Any number of suitable oils are known and may be selected for inclusion in vaccine compositions and immunological adjuvant compositions based on the present disclosure. Examples of such oils, by way of illustration and not limitation, include squalene, squalane, mineral oil, olive oil, cholesterol, and a mannide monooleate.

Immune response modifiers such as imidazoquinoline immune response modifiers are also known in the art and may also be included as adjuvants or co-adjuvants in certain presently disclosed embodiments.

As also noted above, one type of adjuvant or co-adjuvant for use in a vaccine composition according to the disclosure as described herein may be the aluminum co-adjuvants, which are generally referred to as "alum." Alum co-adjuvants are based on the following: aluminum oxy-hydroxide; aluminum hydroxyphosphoate; or various proprietary salts. Alum co-adjuvants are be advantageous because they have a good safety record, augment antibody responses, stabilize antigens, and are relatively simple for large-scale production. (Edelman 2002 Mol. Biotechnol. 21:129-148; Edelman, R. 1980 Rev. Infect. Dis. 2:370-383.)

Pharmaceutical Compositions

In certain illustrative embodiments, the pharmaceutical composition is a vaccine composition that comprises both the recombinant protein according to the disclosure and may further comprise one or more components, as provided herein, that are selected from TLR agonist, co-adjuvant (including, e.g., a cytokine, an imidazoquinoline immune response modifier and/or a dSLIM) and the like and/or a recombinant expression construct, in combination with a pharmaceutically acceptable carrier, excipient or diluent.

Illustrative carriers will be nontoxic to recipients at the dosages and concentrations employed. For vaccines comprising recombinant protein, about 0.01.mu.g/kg to about 100 mg/kg body weight will be administered, typically by the intradermal, subcutaneous, intramuscular or intravenous route, or by other routes.

It will be evident to those skilled in the art that the number and frequency of administration will be dependent upon the response of the host. "Pharmaceutically acceptable carriers" for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, ascorbic acid and esters of p-hydroxybenzoic acid may be added as preservatives. In addition, antioxidants and suspending agents may be used.

The pharmaceutical compositions may be in any form which allows for the composition to be administered to a patient. For example, the composition may be in the form of a solid, liquid or gas (aerosol). Typical routes of administration include, without limitation, oral, topical, parenteral (e.g., sublingually or buccally), sublingual, rectal, vaginal, and intranasal (e.g., as a spray). The term parenteral as used herein includes iontophoretic sonophoretic, passive transdermal, microneedle administration and also subcutaneous injections, intravenous, intramuscular, intrasternal, intracavernous, intrathecal, intrameatal, intraurethral injection or infusion techniques. In a particular embodiment, a composition as described herein (including vaccine and pharmaceutical compositions) is administered intradermally by a technique selected from iontophoresis, microcavitation, sonophoresis or microneedles.

The pharmaceutical composition is formulated so as to allow the active ingredients contained therein to be bioavailable upon administration of the composition to a patient. Compositions that will be administered to a patient take the form of one or more dosage units, where for example, a tablet may be a single dosage unit, and a container of one or more compounds of the invention in aerosol form may hold a plurality of dosage units.

For oral administration, an excipient and/or binder may be present. Examples are sucrose, kaolin, glycerin, starch dextrins, sodium alginate, carboxymethylcellulose and ethyl cellulose. Coloring and/or flavoring agents may be present. A coating shell may be employed.

The composition may be in the form of a liquid, e.g., an elixir, syrup, solution, emulsion or suspension. The liquid may be for oral administration or for delivery by injection, as two examples. When intended for oral administration, preferred compositions contain one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

A liquid pharmaceutical composition as used herein, whether in the form of a solution, suspension or other like form, may include one or more of the following carriers or excipients: sterile diluents such as water for injection, saline solution, preferably physiological saline, Ringer's solution, isotonic sodium chloride, fixed oils such as squalene, squalane, mineral oil, a mannide monooleate, cholesterol, and/or synthetic mono or digylcerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is preferably sterile.

In a particular embodiment, a pharmaceutical or vaccine composition of the invention comprises a stable aqueous suspension of less than 0.2 um and further comprises at least one component selected from the group consisting of phospholipids, fatty acids, surfactants, detergents, saponins, fluorodated lipids, and the like.

It may also be desirable to include other components in a vaccine or pharmaceutical composition, such as delivery vehicles including but not limited to aluminum salts, water-in-oil emulsions, biodegradable oil vehicles, oil-in-water emulsions, biodegradable microcapsules, and liposomes. Examples of additional immunostimulatory substances (co-adjuvants) for use in such vehicles are also described above and may include N-acetylmuramyl-L-alanine-D-isoglutamine (MDP), glucan, IL-12, GM-CSF, gamma interferon and IL-12.

While any suitable carrier known to those of ordinary skill in the art may be employed in the pharmaceutical compositions of this invention, the type of carrier will vary depending on the mode of administration and whether a sustained release is desired. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention.

Pharmaceutical compositions may also contain diluents such as buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Preferably, product may be formulated as a lyophilizate using appropriate excipient solutions (e.g., sucrose) as diluents.

In an illustrative embodiment, the epitope or receptor supporting domain of the recombinant protein, whether derived from a natural or synthetic polypeptide sequence, should have the capacity to self-assemble into oligomeric multimers under appropriate chemical/environmental conditions, or to be reduced to monomers under alternative conditions. Ideally, multimerisation domains will assemble into stable multimers with a discreet number of sub-units, for example dimers, trimers, tetramers, pentamers, etc., such that a product of homogeneous size is generated. Examples of natural polypeptides include, but are not limited to, leucine zippers, lac repressor protein, streptavidin/avidin, cholera toxin B sub-unit, Pseudomonas trimerization domain, and viral capsid proteins.

In an illustrative embodiment, a process of preparing a multivalent molecule is disclosed. In this illustrative embodiment, the process includes assembling multimers from monomeric sub-units to form a synthetic protein including one or more tumor antigens, receptors, and/or a growth factors or parts thereof.

In another illustrative embodiment, a process of preparing a vaccine formulation is disclosed. In this illustrative embodiment, the process includes mixing one or more single monovalent multimers together preparing a multivalent vaccine including a recombinant protein including one or more tumor antigens, receptors, and/or a growth factors or parts thereof.

In yet another illustrative embodiment, a process for treating a patient is disclosed. In this illustrative embodiment, the process includes administering separately to the patient one or more monovalent, one tumor antigen, receptor, and/or growth factor, recombinant proteins in a same day or at alternate days or times during a vaccination period.

While the recombinant protein is described as including or expressing one or more of all or a portion of at least one sequence of the tumor antigens, the growth factors, and/or the receptors, and the CT-B sequence, the recombinant protein may include the natural CT-B sequence or a sequence substantially similar to the natural CT-B sequence and/or a synthetic sequence.

While the recombinant protein is described as including or expressing the CT-B sequence, the recombinant protein may include or express a derivation of the CT-B sequence or a sequence that is substantially similar to the CT-B sequence.

While the homogeneous recombinant proteins expressing or incorporating one or more tumor antigens, growth factors, and/or receptors have been described and illustrated in connection with certain embodiments, many variations and modifications will be evident to those skilled in the art and may be made without departing from the spirit and scope of the disclosure. The disclosure is thus not to be limited to the precise details of methodology or construction set forth above as such variations and modification are intended to be included within the scope of the disclosure.

What is claimed is:

1. A recombinant protein, comprising:
   an immunogenic polypeptide sequence including cholera toxin B subunit (CT-B) or E. coli heat-labile LT B subunit (LT-B);
   a peptide spacer configured to reduce steric hindrance; and
   a polypeptide sequence comprising amino acids 11 to 36 of SEQ ID NO: 38;
   wherein said polypeptide sequence is separated from said immunogenic polypeptide sequence by said peptide spacer within the recombinant protein.

2. The recombinant protein according to claim 1, wherein the peptide spacer is selected from the group consisting of SSGGGSGG (SEQ ID NO: 8), SSGGGGSGGG (SEQ ID NO: 9), TSGGGSG (SEQ ID NO: 10), TSGGGGSGG (SEQ ID NO: 11), SSGGGSGGSSG (SEQ ID NO: 12), GGSGGTSGGGSG (SEQ ID NO: 13), SGGTSGGGGSGG (SEQ ID NO: 14), GGSGGTSGGGGSGG (SEQ ID NO: 15), SSGGGGSGGGSSG (SEQ ID NO: 16), SSGGGSGGSSGGG (SEQ ID NO: 17), SSGGGGSGGGSSGGG (SEQ ID NO: 18), and GGSGGTRPSTAATS (SEQ ID NO: 19).

3. The recombinant protein according to claim 1, wherein the immunogenic polypeptide sequence further comprises a sequence comprising at least a portion of a tumor antigen.

4. The recombinant protein according to claim 1, wherein the immunogenic polypeptide sequence further comprises a sequence comprising at least a portion of a receptor.

5. The recombinant protein according to claim 1, wherein the immunogenic polypeptide sequence further comprises a sequence comprising at least a portion of a tumor antigen and a sequence comprising at least a portion of a receptor.

6. The recombinant protein according to claim 1, comprising a full length or a portion of at least two different growth factors.

7. The recombinant protein according to claim 1, comprising a full length or a portion of one or more growth factors in said protein as a single domain or as two or more tandem repeats.

8. The recombinant protein according to claim 6, comprising a full length or a portion of one or more of the following growth factors: IGF-1, IGF-2, FGF1, FGF2, TGF-α, TGF-β, VEGF-A, VEGF-B, VEGF-C, VEGF-D, PDGF, NGF, EGF, HGF, BMP's, and IL's 1-6.

9. The recombinant protein according to claim 3, wherein said at least a portion of said tumor antigen includes a full length or a portion of two to four different tumor antigens, or a full length or a portion of one or more tumor antigens present as single epitopes or as two or more tandem repeats.

10. The recombinant protein of claim 5, wherein said at least a portion of said receptor includes a full length or part thereof of Human Epidermal growth factor Receptor 2 (Her 2) or Human Epidermal growth factor Receptor 3 (Her 3).

11. The recombinant protein of claim 5 wherein said full length or portion of said receptor includes a full length or portion of two to four different receptors, or a full length or portion of one or more receptors as single epitopes or as two or more tandem repeats.

12. A process of preparing a multivalent molecule comprising:
    assembling multimers from one or more recombinant proteins according to claim 1.

* * * * *

SEQUENCE LISTING

```
<160> NUMBER OF SEQ ID NOS: 47

<210> SEQ ID NO 1
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Met Tyr Ile Glu Ala Leu Asp Lys Tyr Ala
1               5                   10

<210> SEQ ID NO 2
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Ser Leu Ala Gly Ser Ser Gly Ala Leu Ser Lys
1               5                   10

<210> SEQ ID NO 3
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Gly Gly Ser Gly Gly
1               5

<210> SEQ ID NO 4
```

```
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Ser Ser Gly Gly Gly
1               5

<210> SEQ ID NO 5
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 5

His His His His His His
1               5

<210> SEQ ID NO 6
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gly Gly Gly Gly Ser
1               5

<210> SEQ ID NO 7
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Gly Ser Ser Gly
1

<210> SEQ ID NO 8
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Ser Ser Gly Gly Gly Ser Gly Gly
1               5

<210> SEQ ID NO 9
<211> LENGTH: 10
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 9

Ser Ser Gly Gly Gly Gly Ser Gly Gly Gly
1               5                   10

<210> SEQ ID NO 10
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Thr Ser Gly Gly Gly Ser Gly
1               5

<210> SEQ ID NO 11
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Thr Ser Gly Gly Gly Gly Ser Gly Gly
1               5

<210> SEQ ID NO 12
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Ser Ser Gly Gly Gly Ser Gly Gly Ser Ser Gly
1               5                   10

<210> SEQ ID NO 13
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Gly Gly Ser Gly Gly Thr Ser Gly Gly Gly Ser Gly
1               5                   10

<210> SEQ ID NO 14
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 14

Ser Gly Gly Thr Ser Gly Gly Gly Ser Gly Gly
1               5                   10

<210> SEQ ID NO 15
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Gly Gly Ser Gly Gly Thr Ser Gly Gly Gly Ser Gly Gly
1               5                   10

<210> SEQ ID NO 16
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Ser Ser Gly Gly Gly Gly Ser Gly Gly Gly Ser Ser Gly
1               5                   10

<210> SEQ ID NO 17
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Ser Ser Gly Gly Gly Ser Gly Gly Ser Ser Gly Gly Gly
1               5                   10

<210> SEQ ID NO 18
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Ser Ser Gly Gly Gly Gly Ser Gly Gly Gly Ser Ser Gly Gly Gly
1               5                   10                  15

<210> SEQ ID NO 19
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Gly Gly Ser Gly Gly Thr Arg Pro Ser Thr Ala Ala Thr Ser
1               5                   10
```

<210> SEQ ID NO 20
<211> LENGTH: 180
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 20

```
His His His His His His Ile Glu Gly Arg Asn Ser Asp Ser Glu Cys
1               5                   10                  15

Pro Leu Ser His Asp Gly Tyr Cys Leu His Asp Gly Val Cys Met Tyr
            20                  25                  30

Ile Glu Ala Leu Asp Lys Tyr Ala Cys Asn Cys Val Val Gly Tyr Ile
        35                  40                  45

Gly Glu Arg Cys Gln Tyr Arg Asp Leu Lys Trp Trp Glu Leu Arg Gly
    50                  55                  60

Gly Ser Gly Gly Thr Ser Gly Gly Gly Ser Gly Gly Thr Pro Gln
65                  70                  75                  80

Asn Ile Thr Asp Leu Cys Ala Glu Tyr His Asn Thr Gln Ile His Thr
                85                  90                  95

Leu Asn Asp Lys Ile Phe Ser Tyr Thr Glu Ser Leu Ala Gly Lys Arg
            100                 105                 110

Glu Met Ala Ile Ile Thr Phe Lys Asn Gly Ala Thr Phe Gln Val Glu
        115                 120                 125

Val Pro Gly Ser Gln His Ile Asp Ser Gln Lys Lys Ala Ile Glu Arg
    130                 135                 140

Met Lys Asp Thr Leu Arg Ile Ala Tyr Leu Thr Glu Ala Lys Val Glu
145                 150                 155                 160

Lys Leu Cys Val Trp Asn Asn Lys Thr Pro His Ala Ile Ala Ala Ile
                165                 170                 175

Ser Met Ala Asn
            180
```

<210> SEQ ID NO 21
<211> LENGTH: 53
<212> TYPE: PRT
<213> ORGANISM: Homo sapiens

<400> SEQUENCE: 21

```
Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50
```

<210> SEQ ID NO 22
<211> LENGTH: 53
<212> TYPE: PRT
<213> ORGANISM: Pan troglodytes

<400> SEQUENCE: 22

```
Asn Ser Asp Ser Glu Cys Pro Leu Ser His Asp Gly Tyr Cys Leu His
1               5                   10                  15
```

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50

<210> SEQ ID NO 23
<211> LENGTH: 53
<212> TYPE: PRT
<213> ORGANISM: Macaca sp.

<400> SEQUENCE: 23

Asn Ser Asp Ser Gly Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50

<210> SEQ ID NO 24
<211> LENGTH: 53
<212> TYPE: PRT
<213> ORGANISM: Rattus norvegicus

<400> SEQUENCE: 24

Asn Ser Asn Thr Gly Cys Pro Pro Ser Tyr Asp Gly Tyr Cys Leu Asn
1               5                   10                  15

Gly Gly Val Cys Met Tyr Val Glu Ser Val Asp Arg Tyr Val Cys Asn
            20                  25                  30

Cys Val Ile Gly Tyr Ile Gly Glu Arg Cys Gln His Arg Asp Leu Arg
        35                  40                  45

Trp Trp Lys Leu Arg
    50

<210> SEQ ID NO 25
<211> LENGTH: 33
<212> TYPE: PRT
<213> ORGANISM: Rattus rattus

<400> SEQUENCE: 25

Met Tyr Val Glu Ser Val Asp Arg Tyr Val Cys Asn Cys Val Ile Gly
1               5                   10                  15

Tyr Ile Gly Glu Arg Cys Gln His Arg Asp Leu Arg Trp Trp Asn Trp
            20                  25                  30

Arg

<210> SEQ ID NO 26
<211> LENGTH: 53
<212> TYPE: PRT
<213> ORGANISM: Mus musculus

<400> SEQUENCE: 26

Asn Ser Tyr Pro Gly Cys Pro Ser Ser Tyr Asp Gly Tyr Cys Leu Asn
1               5                   10                  15

Gly Gly Val Cys Met His Ile Glu Ser Leu Asp Ser Tyr Thr Cys Asn
            20                  25                  30

Cys Val Ile Gly Tyr Ser Gly Asp Arg Cys Gln Thr Arg Asp Leu Arg
            35                  40                  45

Trp Trp Glu Leu Arg
    50

<210> SEQ ID NO 27
<211> LENGTH: 53
<212> TYPE: PRT
<213> ORGANISM: Sus scrofa

<400> SEQUENCE: 27

Asn Ser Tyr Ser Glu Cys Pro Pro Ser His Asp Gly Tyr Cys Leu His
1               5                   10                  15

Gly Gly Val Cys Met Tyr Ile Glu Ala Val Asp Ser Tyr Ala Cys Asn
            20                  25                  30

Cys Val Phe Gly Tyr Val Gly Glu Arg Cys Gln His Arg Asp Leu Lys
            35                  40                  45

Trp Trp Glu Leu Arg
    50

<210> SEQ ID NO 28
<211> LENGTH: 52
<212> TYPE: PRT
<213> ORGANISM: Felis catus

<400> SEQUENCE: 28

Asn Ser Tyr Gln Glu Cys Pro Pro Ser Tyr Asp Gly Tyr Cys Leu Tyr
1               5                   10                  15

Asn Gly Val Cys Met Tyr Ile Glu Ala Val Asp Arg Tyr Ala Cys Asn
            20                  25                  30

Cys Val Phe Gly Tyr Val Gly Glu Arg Cys Gln His Arg Asp Leu Lys
            35                  40                  45

Trp Glu Leu Arg
    50

<210> SEQ ID NO 29
<211> LENGTH: 52
<212> TYPE: PRT
<213> ORGANISM: Canis lupus

<400> SEQUENCE: 29

Asn Gly Tyr Arg Glu Cys Pro Ser Ser Tyr Asp Gly Tyr Cys Leu Tyr
1               5                   10                  15

Asn Gly Val Cys Met Tyr Ile Glu Ala Val Asp Arg Tyr Ala Cys Asn
            20                  25                  30

Cys Val Phe Gly Tyr Val Gly Glu Arg Cys Gln His Arg Asp Leu Lys
            35                  40                  45

Trp Glu Leu Arg
    50

<210> SEQ ID NO 30
<211> LENGTH: 53
<212> TYPE: PRT
<213> ORGANISM: Equus caballus

<400> SEQUENCE: 30

Asn Ser Tyr Gln Glu Cys Ser Gln Ser Tyr Asp Gly Tyr Cys Leu His
1               5                   10                  15

Gly Gly Lys Cys Val Tyr Leu Val Gln Val Asp Thr His Ala Cys Asn

```
            20                  25                  30

Cys Val Val Gly Tyr Val Gly Glu Arg Cys Gln His Gln Asp Leu Arg
        35                  40                  45

Trp Trp Glu Leu Arg
    50

<210> SEQ ID NO 31
<211> LENGTH: 48
<212> TYPE: PRT
<213> ORGANISM: Taeniopygia guttata

<400> SEQUENCE: 31

Cys Pro Pro Ser Tyr Glu Ser Tyr Cys Leu His Gly Gly Val Cys Asn
1               5                   10                  15

Tyr Val Ser Asp Leu Gln Asp Tyr Ala Cys Asn Cys Val Thr Gly Tyr
            20                  25                  30

Val Gly Glu Arg Cys Gln Phe Ser Asp Leu Glu Trp Trp Glu Gln Arg
        35                  40                  45

<210> SEQ ID NO 32
<211> LENGTH: 46
<212> TYPE: PRT
<213> ORGANISM: Gallus gallus

<400> SEQUENCE: 32

Cys Pro Pro Ala Tyr Asp Ser Tyr Cys Leu His Gly Gly Val Cys Asn
1               5                   10                  15

Tyr Val Ser Asp Leu Gln Asp Tyr Ala Cys Asn Cys Val Thr Gly Tyr
            20                  25                  30

Val Gly Glu Arg Cys Gln Phe Ser Asp Leu Glu Trp Trp Glu
        35                  40                  45

<210> SEQ ID NO 33
<211> LENGTH: 47
<212> TYPE: PRT
<213> ORGANISM: Xenopus sp.

<400> SEQUENCE: 33

Glu Cys Pro Leu Ala Tyr Asp Gly Tyr Cys Leu Asn Gly Gly Val Cys
1               5                   10                  15

Ile His Phe Pro Glu Leu Lys Asp Tyr Gly Cys Arg Cys Val Ala Gly
            20                  25                  30

Tyr Val Gly Glu Arg Cys Gln Phe Asp Asp Leu Lys Ser Trp Glu
        35                  40                  45

<210> SEQ ID NO 34
<211> LENGTH: 53
<212> TYPE: PRT
<213> ORGANISM: Danio rerio

<400> SEQUENCE: 34

Asn Gly Val Gln Ser Cys Pro Ser Thr His Asp Ser Tyr Cys Leu Tyr
1               5                   10                  15

Asp Gly Val Cys Phe Tyr Phe Pro Glu Met Glu Ser Tyr Ala Cys Asn
            20                  25                  30

Cys Val Leu Gly Tyr Met Gly Glu Arg Cys Gln Phe Ser Asp Leu Glu
        35                  40                  45

Trp Trp Glu Leu Gln
    50
```

<210> SEQ ID NO 35
<211> LENGTH: 38
<212> TYPE: PRT
<213> ORGANISM: Branchiostoma sp.

<400> SEQUENCE: 35

Cys Pro Pro Arg Tyr Glu Gly Phe Cys Leu His Gly Gly Ile Cys Phe
1               5                   10                  15

Tyr Val Asp Arg Leu Gly Val Gly Cys Ser Cys Pro Val Met Tyr Glu
            20                  25                  30

Gly Glu Arg Cys Gln Tyr
        35

<210> SEQ ID NO 36
<211> LENGTH: 225
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

His His His His His Ile Glu Gly Arg Asn Ser Asp Ser Glu Cys
1               5                   10                  15

Pro Leu Ser His Asp Gly Tyr Cys Leu His Asp Gly Val Cys Met Tyr
            20                  25                  30

Ile Glu Ala Leu Asp Lys Tyr Ala Cys Asn Cys Val Val Gly Tyr Ile
        35                  40                  45

Gly Glu Arg Cys Gln Tyr Arg Asp Leu Lys Trp Trp Glu Leu Arg Ser
    50                  55                  60

Gly Gly Thr Pro Gln Asn Ile Thr Asp Leu Cys Ala Glu Tyr His Asn
65                  70                  75                  80

Thr Gln Ile His Thr Leu Asn Asp Lys Ile Phe Ser Tyr Thr Glu Ser
                85                  90                  95

Leu Ala Gly Lys Arg Glu Met Ala Ile Ile Thr Phe Lys Asn Gly Ala
            100                 105                 110

Thr Phe Gln Val Glu Val Pro Gly Ser Gln His Ile Asp Ser Gln Lys
        115                 120                 125

Lys Ala Ile Glu Arg Met Lys Asp Thr Leu Arg Ile Ala Tyr Leu Thr
    130                 135                 140

Glu Ala Lys Val Glu Lys Leu Cys Val Trp Asn Asn Lys Thr Pro His
145                 150                 155                 160

Ala Ile Ala Ala Ile Ser Met Ala Asn Ser Ser Gly Asn Ser Asp Ser
                165                 170                 175

Glu Cys Pro Leu Ser His Asp Gly Tyr Cys Leu His Asp Gly Val Cys
            180                 185                 190

Met Tyr Ile Glu Ala Leu Asp Lys Tyr Ala Cys Asn Cys Val Val Gly
        195                 200                 205

Tyr Ile Gly Glu Arg Cys Gln Tyr Arg Asp Leu Lys Trp Trp Glu Leu
    210                 215                 220

Arg
225

<210> SEQ ID NO 37
<211> LENGTH: 139
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 37

His His His His His His Ile Glu Gly Arg Cys Met Tyr Ile Glu Ala
1               5                   10                  15

Leu Asp Lys Tyr Ser Gly Gly Thr Pro Gln Asn Ile Thr Asp Leu Cys
            20                  25                  30

Ala Glu Tyr His Asn Thr Gln Ile His Thr Leu Asn Asp Lys Ile Phe
        35                  40                  45

Ser Tyr Thr Glu Ser Leu Ala Gly Lys Arg Glu Met Ala Ile Ile Thr
50                  55                  60

Phe Lys Asn Gly Ala Thr Phe Gln Val Glu Val Pro Gly Ser Gln His
65                  70                  75                  80

Ile Asp Ser Gln Lys Lys Ala Ile Glu Arg Met Lys Asp Thr Leu Arg
                85                  90                  95

Ile Ala Tyr Leu Thr Glu Ala Lys Val Glu Lys Leu Cys Val Trp Asn
            100                 105                 110

Asn Lys Thr Pro His Ala Ile Ala Ala Ile Ser Met Ala Asn Ser Ser
        115                 120                 125

Gly Cys Met Tyr Ile Glu Ala Leu Asp Lys Tyr
    130                 135

<210> SEQ ID NO 38
<211> LENGTH: 171
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

His His His His His His Ile Glu Gly Arg Cys Pro Leu Ser His Asp
1               5                   10                  15

Gly Tyr Cys Leu His Asp Gly Val Cys Met Tyr Ile Glu Ala Leu Asp
            20                  25                  30

Lys Tyr Ala Cys Ser Gly Gly Thr Pro Gln Asn Ile Thr Asp Leu Cys
        35                  40                  45

Ala Glu Tyr His Asn Thr Gln Ile His Thr Leu Asn Asp Lys Ile Phe
    50                  55                  60

Ser Tyr Thr Glu Ser Leu Ala Gly Lys Arg Glu Met Ala Ile Ile Thr
65                  70                  75                  80

Phe Lys Asn Gly Ala Thr Phe Gln Val Glu Val Pro Gly Ser Gln His
                85                  90                  95

Ile Asp Ser Gln Lys Lys Ala Ile Glu Arg Met Lys Asp Thr Leu Arg
            100                 105                 110

Ile Ala Tyr Leu Thr Glu Ala Lys Val Glu Lys Leu Cys Val Trp Asn
        115                 120                 125

Asn Lys Thr Pro His Ala Ile Ala Ala Ile Ser Met Ala Asn Ser Ser
    130                 135                 140

Gly Cys Pro Leu Ser His Asp Gly Tyr Cys Leu His Asp Gly Val Cys
145                 150                 155                 160

Met Tyr Ile Glu Ala Leu Asp Lys Tyr Ala Cys
                165                 170
```

```
<210> SEQ ID NO 39
<211> LENGTH: 253
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

His His His His His His Ile Glu Gly Arg Gly Pro Glu Thr Leu Cys
1               5                   10                  15

Gly Ala Glu Leu Val Asp Ala Leu Gln Phe Val Cys Gly Asp Arg Gly
            20                  25                  30

Phe Tyr Phe Asn Lys Pro Thr Gly Tyr Gly Ser Ser Ser Arg Arg Ala
        35                  40                  45

Pro Gln Thr Gly Ile Val Asp Glu Cys Cys Phe Arg Ser Cys Asp Leu
    50                  55                  60

Arg Arg Leu Glu Met Tyr Cys Ala Pro Leu Lys Pro Ala Lys Ser Ala
65                  70                  75                  80

Gly Ser Ser Gly Asn Ser Asp Ser Glu Cys Pro Leu Ser His Asp Gly
                85                  90                  95

Tyr Cys Leu His Asp Gly Val Cys Met Tyr Ile Glu Ala Leu Asp Lys
            100                 105                 110

Tyr Ala Cys Asn Cys Val Val Gly Tyr Ile Gly Glu Arg Cys Gln Tyr
        115                 120                 125

Arg Asp Leu Lys Trp Trp Glu Leu Arg Gly Ser Gly Gly Thr Ser
    130                 135                 140

Gly Gly Gly Gly Ser Gly Thr Pro Gln Asn Ile Thr Asp Leu Cys
145                 150                 155                 160

Ala Glu Tyr His Asn Thr Gln Ile His Thr Leu Asn Asp Lys Ile Phe
                165                 170                 175

Ser Tyr Thr Glu Ser Leu Ala Gly Lys Arg Glu Met Ala Ile Ile Thr
            180                 185                 190

Phe Lys Asn Gly Ala Thr Phe Gln Val Glu Val Pro Ser Gln His Ile
        195                 200                 205

Asp Ser Gln Lys Lys Ala Ile Glu Arg Met Lys Asp Thr Leu Arg Ile
    210                 215                 220

Ala Tyr Leu Thr Glu Ala Lys Val Glu Lys Leu Cys Val Trp Asn Asn
225                 230                 235                 240

Lys Thr Pro His Ala Ile Ala Ala Ile Ser Met Ala Asn
                245                 250

<210> SEQ ID NO 40
<211> LENGTH: 185
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

His His His His His His Ile Glu Gly Arg Thr Pro Gln Asn Ile Thr
1               5                   10                  15

Asp Leu Cys Ala Glu Tyr His Asn Thr Gln Ile His Thr Leu Asn Asp
            20                  25                  30

Lys Ile Phe Ser Tyr Thr Glu Ser Leu Ala Gly Lys Arg Glu Met Ala
```

```
                35                  40                  45
Ile Ile Thr Phe Lys Asn Gly Ala Thr Phe Gln Val Glu Val Pro Ser
 50                  55                  60

Gln His Ile Asp Ser Gln Lys Lys Ala Ile Glu Arg Met Lys Asp Thr
 65                  70                  75                  80

Leu Arg Ile Ala Tyr Leu Thr Glu Ala Lys Val Glu Lys Leu Cys Val
                 85                  90                  95

Trp Asn Asn Lys Thr Pro His Ala Ile Ala Ile Ser Met Ala Asn
                100                 105                 110

Ser Ser Gly Gly Pro Glu Thr Leu Cys Gly Ala Glu Leu Val Asp Ala
            115                 120                 125

Leu Gln Phe Val Cys Gly Asp Arg Gly Phe Tyr Phe Asn Lys Pro Thr
130                 135                 140

Gly Tyr Gly Ser Ser Ser Arg Arg Ala Pro Gln Thr Gly Ile Val Asp
145                 150                 155                 160

Glu Cys Cys Phe Arg Ser Cys Asp Leu Arg Arg Leu Glu Met Tyr Cys
                165                 170                 175

Ala Pro Leu Lys Pro Ala Lys Ser Ala
                180                 185

<210> SEQ ID NO 41
<211> LENGTH: 228
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

His His His His His His Ile Glu Gly Arg Thr Pro Gln Asn Ile Thr
 1               5                  10                  15

Asp Leu Cys Ala Glu Tyr His Asn Thr Gln Ile His Thr Leu Asn Asp
                20                  25                  30

Lys Ile Phe Ser Tyr Thr Glu Ser Leu Ala Gly Lys Arg Glu Met Ala
            35                  40                  45

Ile Ile Thr Phe Lys Asn Gly Ala Thr Phe Gln Val Glu Val Pro Gly
 50                  55                  60

Ser Gln His Ile Asp Ser Gln Lys Lys Ala Ile Glu Arg Met Lys Asp
 65                  70                  75                  80

Thr Leu Arg Ile Ala Tyr Leu Thr Glu Ala Lys Val Glu Lys Leu Cys
                 85                  90                  95

Val Trp Asn Asn Lys Thr Pro His Ala Ile Ala Ala Ile Ser Met Ala
                100                 105                 110

Asn Ser Ser Gly Ala Leu Asp Thr Asn Tyr Cys Phe Ser Ser Thr Glu
            115                 120                 125

Lys Asn Cys Cys Val Arg Gln Leu Tyr Ile Asp Phe Arg Lys Asp Leu
130                 135                 140

Gly Trp Lys Trp Ile His Glu Pro Lys Gly Tyr His Ala Asn Phe Cys
145                 150                 155                 160

Leu Gly Pro Cys Pro Tyr Ile Trp Ser Leu Asp Thr Gln Tyr Ser Lys
                165                 170                 175

Val Leu Ala Leu Tyr Asn Gln His Asn Pro Gly Ala Ser Ala Ser Pro
                180                 185                 190

Cys Cys Val Pro Gln Ala Leu Glu Pro Leu Pro Ile Val Tyr Tyr Val
            195                 200                 205
```

```
Gly Arg Lys Pro Lys Val Glu Gln Leu Ser Asn Met Ile Val Arg Ser
            210                 215                 220

Cys Lys Cys Ser
225

<210> SEQ ID NO 42
<211> LENGTH: 261
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

His His His His His Ile Glu Gly Arg Thr Pro Gln Asn Ile Thr
 1               5                  10                  15

Asp Leu Cys Ala Glu Tyr His Asn Thr Gln Ile His Thr Leu Asn Asp
                20                  25                  30

Lys Ile Phe Ser Tyr Thr Glu Ser Leu Ala Gly Lys Arg Glu Met Ala
            35                  40                  45

Ile Ile Thr Phe Lys Asn Gly Ala Thr Phe Gln Val Glu Val Pro Gly
        50                  55                  60

Ser Gln His Ile Asp Ser Gln Lys Lys Ala Ile Glu Arg Met Lys Asp
65                  70                  75                  80

Thr Leu Arg Ile Ala Tyr Leu Thr Glu Ala Lys Val Glu Lys Leu Cys
                85                  90                  95

Val Trp Asn Asn Lys Thr Pro His Ala Ile Ala Ala Ile Ser Met Ala
            100                 105                 110

Asn Ser Ser Gly Pro Ala Leu Pro Glu Asp Gly Gly Ala Ala Phe Pro
        115                 120                 125

Pro Gly His Phe Lys Asp Pro Lys Arg Leu Tyr Cys Lys Asn Gly Gly
    130                 135                 140

Phe Phe Leu Arg Ile His Pro Asp Gly Arg Val Asp Gly Val Arg Glu
145                 150                 155                 160

Lys Ser Asp Pro His Val Lys Leu Gln Leu Gln Ala Glu Glu Arg Gly
                165                 170                 175

Val Val Ser Ile Lys Gly Val Cys Ala Asn Arg Tyr Leu Ala Met Lys
            180                 185                 190

Glu Asp Gly Arg Leu Leu Ala Ser Lys Cys Val Thr Glu Glu Cys Phe
        195                 200                 205

Phe Phe Glu Arg Leu Glu Ser Asn Asn Tyr Asn Thr Tyr Arg Ser Arg
    210                 215                 220

Lys Tyr Ser Ser Trp Tyr Val Ala Leu Lys Arg Thr Gly Gln Tyr Lys
225                 230                 235                 240

Leu Gly Ser Lys Thr Gly Pro Gly Gln Lys Ala Ile Leu Phe Leu Pro
                245                 250                 255

Met Ser Ala Lys Ser
            260

<210> SEQ ID NO 43
<211> LENGTH: 299
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 43

```
His His His His His Gln Lys Lys Arg Asn Thr Leu His Glu
1               5                   10                  15

Phe Lys Lys Ser Ala Lys Thr Thr Leu Thr Lys Glu Asp Pro Leu Leu
                20                  25                  30

Lys Ile Lys Thr Lys Lys Val Asn Ser Ala Asp Glu Cys Ala Asn Arg
            35                  40                  45

Cys Ile Arg Asn Arg Gly Phe Thr Phe Thr Cys Lys Ala Phe Val Phe
50                  55                  60

Asp Lys Ser Arg Lys Arg Cys Tyr Trp Tyr Pro Phe Asn Ser Met Ser
65                  70                  75                  80

Ser Gly Val Lys Lys Gly Phe Gly His Glu Phe Asp Leu Tyr Glu Asn
                85                  90                  95

Lys Asp Tyr Ile Arg Asn Cys Ile Ile Gly Lys Gly Ser Tyr Lys
            100                 105                 110

Gly Thr Val Ser Ile Thr Lys Ser Gly Ile Lys Cys Gln Pro Trp Asn
            115                 120                 125

Ser Met Ile Pro His Glu His Ser Phe Leu Pro Ser Ser Tyr Arg Gly
130                 135                 140

Lys Asp Leu Gln Glu Asn Tyr Cys Arg Asn Pro Arg Gly Glu Glu Gly
145                 150                 155                 160

Gly Pro Trp Cys Phe Thr Ser Asn Pro Glu Val Arg Tyr Glu Val Cys
                165                 170                 175

Asp Ile Pro Gln Cys Ser Gly Gly Ser Gly Gly Thr Gly Gly Gly
            180                 185                 190

Gly Ser Gly Gly Thr Pro Gln Asn Ile Thr Asp Leu Cys Ala Glu Tyr
        195                 200                 205

His Asn Thr Gln Ile His Thr Leu Asn Asp Lys Ile Phe Ser Tyr Thr
        210                 215                 220

Glu Ser Leu Ala Gly Lys Arg Glu Met Ala Ile Ile Thr Phe Lys Asn
225                 230                 235                 240

Gly Ala Thr Phe Gln Val Glu Val Pro Gly Ser Gln His Ile Asp Ser
                245                 250                 255

Gln Lys Lys Ala Ile Glu Arg Met Lys Asp Thr Leu Arg Ile Ala Tyr
            260                 265                 270

Leu Thr Glu Ala Lys Val Glu Lys Leu Cys Val Trp Asn Asn Lys Thr
            275                 280                 285

Pro His Ala Ile Ala Ile Ser Met Ala Asn
        290                 295
```

<210> SEQ ID NO 44
<211> LENGTH: 256
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 44

```
His His His His His His Ile Glu Gly Arg Thr Pro Gln Asn Ile Thr
1               5                   10                  15

Asp Leu Cys Ala Glu Tyr His Asn Thr Gln Ile His Thr Leu Asn Asp
                20                  25                  30

Lys Ile Phe Ser Tyr Thr Glu Ser Leu Ala Gly Lys Arg Glu Met Ala
```

```
            35                  40                  45
Ile Ile Thr Phe Lys Asn Gly Ala Thr Phe Gln Val Glu Val Pro Gly
        50                  55                  60

Ser Gln His Ile Asp Ser Gln Lys Lys Ala Ile Glu Arg Met Lys Asp
 65                  70                  75                  80

Thr Leu Arg Ile Ala Tyr Leu Thr Glu Ala Lys Val Glu Lys Leu Cys
                85                  90                  95

Val Trp Asn Asn Lys Thr Pro His Ala Ile Ala Ala Ile Ser Met Ala
                100                 105                 110

Asn Ser Ser Gly Gly Pro Glu Thr Leu Cys Gly Ala Glu Leu Val Asp
            115                 120                 125

Ala Leu Gln Phe Val Cys Gly Pro Arg Gly Phe Tyr Phe Asn Lys Pro
        130                 135                 140

Thr Gly Tyr Gly Ser Ser Ile Arg Arg Ala Pro Gln Thr Gly Ile Val
145                 150                 155                 160

Asp Glu Cys Cys Phe Arg Ser Cys Asp Leu Arg Arg Leu Glu Met Tyr
                165                 170                 175

Cys Ala Pro Leu Lys Pro Thr Lys Ala Ala Gly Gly Ser Ala Tyr Gly
                180                 185                 190

Pro Gly Glu Thr Leu Cys Gly Gly Glu Leu Val Asp Thr Leu Gln Phe
            195                 200                 205

Val Cys Ser Asp Arg Gly Phe Tyr Phe Ser Arg Pro Ser Ser Arg Ala
        210                 215                 220

Asn Arg Arg Ser Arg Gly Ile Val Glu Glu Cys Cys Phe Arg Ser Cys
225                 230                 235                 240

Asp Leu Ala Leu Leu Glu Thr Tyr Cys Ala Thr Pro Ala Lys Ser Glu
                245                 250                 255

<210> SEQ ID NO 45
<211> LENGTH: 309
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

His His His His His Ile Glu Gly Arg Thr Pro Gln Asn Ile Thr
 1               5                  10                  15

Asp Leu Cys Ala Glu Tyr His Asn Thr Gln Ile His Thr Leu Asn Asp
                20                  25                  30

Lys Ile Phe Ser Tyr Thr Glu Ser Leu Ala Gly Lys Arg Glu Met Ala
            35                  40                  45

Ile Ile Thr Phe Lys Asn Gly Ala Thr Phe Gln Val Glu Val Pro Gly
        50                  55                  60

Ser Gln His Ile Asp Ser Gln Lys Lys Ala Ile Glu Arg Met Lys Asp
 65                  70                  75                  80

Thr Leu Arg Ile Ala Tyr Leu Thr Glu Ala Lys Val Glu Lys Leu Cys
                85                  90                  95

Val Trp Asn Asn Lys Thr Pro His Ala Ile Ala Ala Ile Ser Met Ala
                100                 105                 110

Asn Ser Ser Gly Val Ile Lys Phe Met Asp Val Tyr Gln Arg Ser Tyr
            115                 120                 125

Cys Arg Pro Ile Glu Thr Leu Val Asp Ile Phe Gln Glu Tyr Pro Asp
        130                 135                 140
```

```
Glu Ile Glu Tyr Ile Phe Lys Pro Ser Cys Val Pro Leu Met Arg Cys
145                 150                 155                 160

Ala Gly Cys Cys Asn Asp Glu Ala Leu Glu Cys Val Pro Thr Ser Glu
            165                 170                 175

Ser Asn Ile Thr Met Gln Ile Met Arg Ile Lys Pro His Gln Ser Gln
        180                 185                 190

His Ile Gly Glu Met Ser Phe Leu Gln His Ser Arg Cys Glu Cys Arg
    195                 200                 205

Pro Lys Lys Thr Glu Ile Leu Lys Ser Ile Asp Asn Glu Trp Arg Lys
210                 215                 220

Thr Gln Cys Met Pro Arg Glu Val Cys Ile Asp Val Gly Lys Glu Phe
225                 230                 235                 240

Gly Ala Ala Thr Asn Thr Phe Phe Lys Pro Pro Cys Val Ser Val Tyr
                245                 250                 255

Arg Cys Gly Gly Cys Cys Asn Ser Glu Gly Leu Gln Cys Met Asn Thr
            260                 265                 270

Ser Thr Gly Tyr Leu Ser Lys Thr Leu Phe Glu Ile Thr Val Pro Leu
        275                 280                 285

Ser Gln Gly Pro Lys Pro Val Thr Ile Ser Phe Ala Asn His Thr Ser
    290                 295                 300

Cys Arg Cys Met Ser
305

<210> SEQ ID NO 46
<211> LENGTH: 234
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

His His His His His Ala Leu Asp Thr Asn Tyr Cys Phe Ser Ser
1               5                   10                  15

Thr Glu Lys Asn Cys Cys Val Arg Gln Leu Tyr Ile Asp Phe Arg Lys
            20                  25                  30

Asp Leu Gly Trp Lys Trp Ile His Glu Pro Lys Gly Tyr His Ala Asn
        35                  40                  45

Phe Cys Leu Gly Pro Cys Pro Tyr Ile Trp Ser Leu Asp Thr Gln Tyr
    50                  55                  60

Ser Lys Val Leu Ala Leu Tyr Asn Gln His Asn Pro Gly Ala Ser Ala
65                  70                  75                  80

Ala Pro Cys Cys Val Pro Gln Ala Leu Glu Pro Leu Pro Ile Val Tyr
                85                  90                  95

Tyr Val Gly Arg Lys Pro Lys Val Glu Gln Leu Ser Asn Met Ile Val
            100                 105                 110

Arg Ser Cys Lys Cys Ser Gly Ser Gly Gly Thr Ser Gly Gly Gly
        115                 120                 125

Gly Gly Ser Gly Thr Pro Gln Asn Ile Thr Asp Leu Cys Ala Glu Tyr
    130                 135                 140

His Asn Thr Gln Ile His Thr Leu Asn Asp Lys Ile Phe Ser Tyr Thr
145                 150                 155                 160

Glu Ser Leu Ala Gly Lys Arg Glu Met Ala Ile Ile Thr Phe Lys Asn
                165                 170                 175
```

```
Gly Ala Thr Phe Gln Val Glu Val Pro Ser Gln His Ile Asp Ser Gln
            180                 185                 190

Lys Lys Ala Ile Glu Arg Met Lys Asp Thr Leu Arg Ile Ala Tyr Leu
        195                 200                 205

Thr Glu Ala Lys Val Glu Lys Leu Cys Val Trp Asn Asn Lys Thr Pro
    210                 215                 220

His Ala Ile Ala Ala Ile Ser Met Ala Asn
225                 230

<210> SEQ ID NO 47
<211> LENGTH: 234
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

His His His His His Ile Glu Gly Arg Ala Val Lys Phe Pro Gln
1               5                   10                  15

Leu Cys Lys Phe Cys Asp Val Arg Phe Ser Thr Cys Asp Asn Gln Lys
            20                  25                  30

Ser Cys Met Ser Asn Cys Ser Ile Thr Ser Ile Cys Glu Lys Pro Gln
            35                  40                  45

Glu Val Cys Val Ala Val Trp Arg Lys Asn Asp Glu Asn Ile Thr Leu
    50                  55                  60

Glu Thr Val Cys His Asp Pro Lys Leu Pro Tyr His Asp Phe Ile Leu
65              70                  75                  80

Glu Asp Ala Ala Ser Pro Lys Cys Ile Met Lys Glu Lys Lys Pro
                85                  90                  95

Gly Glu Thr Phe Phe Met Cys Ser Cys Ser Ser Asp Glu Cys Asn Asp
            100                 105                 110

Asn Ile Ile Phe Ser Glu Gly Gly Ser Gly Gly Thr Ser Gly Gly Gly
            115                 120                 125

Gly Gly Ser Gly Thr Pro Gln Asn Ile Thr Asp Leu Cys Ala Glu Tyr
        130                 135                 140

His Asn Thr Gln Ile His Thr Leu Asn Asp Lys Ile Phe Ser Tyr Thr
145                 150                 155                 160

Glu Ser Leu Ala Gly Lys Arg Glu Met Ala Ile Ile Thr Phe Lys Asn
                165                 170                 175

Gly Ala Thr Phe Gln Val Glu Val Pro Ser Gln His Ile Asp Ser Gln
            180                 185                 190

Lys Lys Ala Ile Glu Arg Met Lys Asp Thr Leu Arg Ile Ala Tyr Leu
        195                 200                 205

Thr Glu Ala Lys Val Glu Lys Leu Cys Val Trp Asn Asn Lys Thr Pro
    210                 215                 220

His Ala Ile Ala Ala Ile Ser Met Ala Asn
225                 230
```